US012797247B2

(12) United States Patent
Wyatt et al.

(10) Patent No.: US 12,797,247 B2
(45) Date of Patent: Nov. 17, 2026

(54) APPARATUS AND METHODS FOR TREATING TINNITUS

(71) Applicant: ST OTO DEVICES, LLC, Nashville, TN (US)

(72) Inventors: Sammi Wyatt, Nashville, TN (US); Todd Huber, Nashville, TN (US)

(73) Assignee: ST OTO DEVICES, LLC, Nashville, TN (US)

( * ) Notice: Subject to any disclaimer, the term of this patent is extended or adjusted under 35 U.S.C. 154(b) by 823 days.

(21) Appl. No.: 18/129,618

(22) Filed: Mar. 31, 2023

(65) Prior Publication Data

US 2023/0310216 A1 Oct. 5, 2023

Related U.S. Application Data

(60) Provisional application No. 63/325,666, filed on Mar. 31, 2022.

(51) Int. Cl.

*A61F 11/00* (2022.01)
*A61H 23/02* (2006.01)
*H04R 25/00* (2006.01)

(52) U.S. Cl.

CPC .............. *A61F 11/00* (2013.01); *A61H 23/02* (2013.01); *H04R 25/505* (2013.01); (Continued)

(58) Field of Classification Search

CPC ........ A61F 11/00–30; A61H 23/00–06; A61H 2201/1604–1607; A61H 2205/027; H04R 25/00–75; H04R 2225/55; H04R 2430/01
See application file for complete search history.

(56) References Cited

U.S. PATENT DOCUMENTS 6,068,590 A 5/2000 Brisken
2007/0249889 A1 10/2007 Hanson et al.
(Continued)

FOREIGN PATENT DOCUMENTS

KR 20090102025 A * 9/2009 ............. H04R 25/50
KR 10-2021-0061261 A 5/2021
(Continued)

OTHER PUBLICATIONS

Translation of KR-20220029838-A. Accessed from PE2E-SAEARCH on Mar. 10, 2026. (Year: 2022).*
(Continued)

*Primary Examiner* — Paige Kathleen Bugg
(74) *Attorney, Agent, or Firm* — Holland & Knight LLP; Matthew C. Cox; Forrest S. Tinnin

(57) ABSTRACT

Systems, methods, and apparatuses to treat subjective tinnitus is disclosed herein. A series of short, self-administered treatments with the apparatus may lessen or eliminate the subjective perception of tinnitus in the majority of individuals. The apparatus that delivers the treatment may include four bone conductors, two for each ear delivering sound to the inner ear via bone conduction. Each ear receives low frequency tones between fifty and one-hundred-and-ten hertz high frequency tones between six-thousand and ten-thousand hertz. The low frequency tones and high frequency tones may be all delivered slightly above an auditory threshold intensity. The apparatus may be self-contained, rechargeable and controllable via mobile phone application. The method of treatment may involve programmed sessions lasting one to fifteen minutes.

18 Claims, 37 Drawing Sheets

(52) U.S. Cl.
CPC ......... *H04R 25/554* (2013.01); *H04R 25/558* (2013.01); *H04R 25/606* (2013.01); *H04R 25/75* (2013.01); *A61H 2201/1607* (2013.01); *A61H 2201/165* (2013.01); *H04R 2225/55* (2013.01); *H04R 2430/01* (2013.01)

(56) References Cited

U.S. PATENT DOCUMENTS

| | | | |
|---|---|---|---|
| 2012/0203130 A1 | 8/2012 | Bernhard | |
| 2019/0344073 A1* | 11/2019 | Baker ................ | A61N 1/37247 |
| 2020/0001085 A1 | 1/2020 | Owen et al. | |
| 2020/0382884 A1* | 12/2020 | Chang .................... | A61H 39/00 |
| 2020/0396529 A1* | 12/2020 | Thomas ............... | H04R 1/1091 |
| 2021/0168545 A1 | 6/2021 | Mandala' et al. | |
| 2021/0219066 A1* | 7/2021 | Zhang .................. | G10K 11/175 |
| 2022/0126094 A1* | 4/2022 | Eagleman .......... | A61H 23/0236 |
| 2023/0264018 A1* | 8/2023 | Tass ..................... | A61H 23/008 607/2 |
| 2024/0244385 A1* | 7/2024 | Marie De Chastenay .................. | H04R 25/606 |

FOREIGN PATENT DOCUMENTS

| | | | | |
|---|---|---|---|---|
| KR | 20210061261 A * | 5/2021 | ............... | H04R 1/10 |
| KR | 10-2022-0029838 A | 3/2022 | | |
| KR | 20220029838 A * | 3/2022 | ............... | A61F 7/02 |
| WO | 2015-020753 A2 | 2/2015 | | |

OTHER PUBLICATIONS

Translation of KR-20210061261-A. Accessed from PE2E-SEARCH on Mar. 10, 2026. (Year: 2021).*

Translation of KR-20090102025-A. Accessed from PE2E-SEARCH on Mar. 10, 2026. (Year: 2009).*

PCT/US2023/065241 International Search Report and Written Opinion, dated Jul. 31, 2023, 12 pages.

Arthur Boothroyd, Ph.D., and Sheila Cawkwell, B.A. "Vibrotactile Thresholds in Pure Tone Audiometry." Acta Oto-Laryngologica 69 Nos. 1-6 (Jul. 1970): 381-387, DOI: 10.3109/00016487009123382.

Martin L. Lenhardt, Barbara A. Goldstein, Abraham Shulman, and Robert Guinta. "Use of High-Frequency and Muscle Vibration in the Treatment of Tinnitus." International Tinnitus Journal 9, No. 1 (2003): 32-36.

Martin L. Lenhardt. "Vibrotactile suppression of tinnitus." The Journal of Acoustical Society of America 111, No. 5 Supplement (May 2002), 1 page: doi:10.1121/1.4777921.

Extended European Office Action issued in related Application Serial No. 23782111.1 on Feb. 2, 2026.

* cited by examiner

310

| First Low Frequency Ocillation Device | | | Second Low Frequency Ocillation Device | | | First High Frequency Ocillation Device | | | Second Hight Frequency Ocillation Device | | |
|---|---|---|---|---|---|---|---|---|---|---|---|
| On/Off | Frequency | Amplitude | On/Off | Frequency | Amplitude | On/Off | Frequency | Amplitude | On/Off | Frequency | Amplitude |
| 1 | 40 Hz | 25 dB | 0 | - | - | 1 | 6 kHz | 30 dB | 1 | 8 kHz | 35 dB |

FIG. 32

APPARATUS AND METHODS FOR TREATING TINNITUS

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

This application is a non-provisional of and claims priority to and benefit of U.S. Patent Application No. 63/325,666 filed Mar. 31, 2022, which is incorporated by reference in its entirety.

STATEMENT REGARDING FEDERALLY SPONSORED RESEARCH OR DEVELOPMENT

Not applicable.

REFERENCE TO SEQUENCE LISTING OR COMPUTER PROGRAM LISTING INDEX

Not applicable.

BACKGROUND

The present invention relates generally to tinnitus. More particularly, the present disclosure pertains to systems, methods, and apparatuses for treating tinnitus.

Tinnitus is an extremely common problem that is generally defined as the perception of noise or ringing in the ears. Tinnitus can be quite troublesome, interfering with mood and concentration, and can cause anxiety, insomnia and depression. Tinnitus may occur in an individual for a number of reasons, but the most common cause is nerve hearing loss. Tinnitus is most commonly perceived by an individual as a high pitch tone, usually in a frequency range of six-thousand to ten-thousand hertz. Other sensations of tinnitus may also be described as a hiss, crickets, cicadas, or a buzzing noise.

Conventional systems may "mask" tinnitus (e.g., abating the individual's perception of tinnitus without necessarily treating the underlying condition of tinnitus). Typical masking systems involve hearing aids used to introduce a narrow band white noise (or brown noise, pink noise, and so on) with the center of the noise at the pitch of the individual's perceived tinnitus (e.g., at approximately six-thousand hertz). While the hearing aid with masking is worn, the individual no longer perceives the tinnitus, or if the individual does perceive the tinnitus, the tinnitus may be significantly reduced in severity. However, when the hearing aid is removed, the individual may immediately perceive his/her tinnitus again. Because individuals do not wear hearing aids while in bed, such conventional systems only treat individuals with "daytime" symptoms of tinnitus. Most individuals experience their worst tinnitus at night. Therefore, such conventional systems fail to address this crucial time for individuals suffering from tinnitus. Moreover, such typical systems for masking tinnitus fail to treat the underlying condition of tinnitus, and therefore are required indefinitely for abating the individual's condition.

Other conventional systems have begun to actually treat tinnitus (e.g., prevent the recurrence of tinnitus symptoms), rather than simply masking the condition. Typical treatment systems involve Tinnitus Retraining Therapy (TRT). The only treatment currently known is Tinnitus Retraining Therapy (TRT). TRT is a time-consuming process generally performed in an audiologist's office involving low-frequency air conduction stimulation as a method to hypothetically prevent the recurrence of tinnitus symptoms. However, such typical systems have a number of problems. As an example, TRT utilizes air conduction and has a low success rate. "Air conduction" typically involves a tone being provided by an earphone or a loudspeaker. The signal travels through the air in the outer ear to the middle ear and then to the cochlea in the inner ear in order to attempt to treat tinnitus. Moreover, such typical systems require visits to a medical practitioner and are therefore inconvenient and not frequent enough to effectively treat tinnitus.

What is needed, therefore, are improved systems, methods, and apparatuses for the treatment of tinnitus. Currently, however, there is no device on the market that offers a rehab component for tinnitus, thereby preventing it from recurring.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present disclosure provides apparatuses, systems and methods for masking and treating tinnitus. One aspect of the disclosure is an apparatus for treating tinnitus. The apparatus may include a semi-circular strap. The semi-circular strap may be configured to be positioned about a rear portion of a head of a user. The apparatus may further include a first over-ear strap. The first over-ear strap may be configured to be positioned over a first ear of the head of the user. The apparatus may further include a second over-ear strap. The second over-ear strap may be configured to be positioned over a second ear of the head of the user. The apparatus may further include a number of bone conductors. The number of bone conductors may include a first low frequency bone conductor. The first low frequency bone conductor may be located between first over-ear strap and the semi-circular strap. The first low frequency bone conductor may be configured to contact the head of the user rearward of the first ear of the user. The number of bone conductors may further include a second low frequency bone conductor. The second low frequency bone conductor may be located between the second over-ear strap and the semi-circular strap. The second low frequency bone conductor may be configured to contact the head of the user rearward of the second ear of the user. The first and second low frequency bone conductors may be configured to generate tones at a frequency of about fifty hertz and about one-hundred-and-ten hertz.

In some embodiments of the present disclosure, the apparatus further includes a first high frequency bone conductor and a second high frequency bone conductor. The first high frequency bone conductor may be located opposite the first low frequency bone conductor relative to the first over-ear strap. The first high frequency bone conductor configured to contact the head of the user forward of the first ear of the user. The second high frequency bone conductor may be located opposite the second low frequency bone conductor relative to the second over-ear strap. The second high frequency bone conductor may be configured to contact the head of the user forward of the second ear of the user. The first and second high frequency bone conductors may be configured to generate tones at a frequency of between about six-thousand hertz and ten-thousand hertz.

Another aspect of the present disclosure is a method of treating tinnitus. The method may include positioning a headset apparatus on a head of a user. The method may further include administering low frequency tones using a first pair of bone conductors of the headset apparatus for a predetermined time period. The low frequency tones may be between about fifty hertz and one-hundred-and-ten hertz. The method may further include simultaneously administering high frequency tones using a second pair of bone conductors of the headset apparatus for the predetermined time period. The high frequency tones may be between about six-thousand hertz and about ten-thousand hertz.

Yet another aspect of the present disclosure is a system for treating tinnitus. The system may include the aforementioned apparatus for treating tinnitus. The system may further include a controller configured to control a volume and a frequency of tones generated by each of the bone conductors of the apparatus. In some embodiments, the controller is located on the apparatus, receives inputs from manual controls located on the apparatus, and controls the apparatus in accordance with the inputs. In other embodiments, the controller is located on a device external to the apparatus, receives inputs from manual controls located on the device, and controls the apparatus in accordance with the inputs via a wired connection. In other embodiments still, the controller is located on the apparatus, wirelessly receives inputs from a mobile device, and controls the apparatus in accordance with the inputs via the wireless connection.

Numerous other objects, advantages and features of the present disclosure will be readily apparent to those of skill in the art upon a review of the following drawings and description of a preferred embodiment.

BRIEF DESCRIPTION OF THE DRAWINGS

FIG. 32 is a schematic diagram of a data packet of the system of FIG. 30 in accordance with the present disclosure.

DETAILED DESCRIPTION

Figure 1:
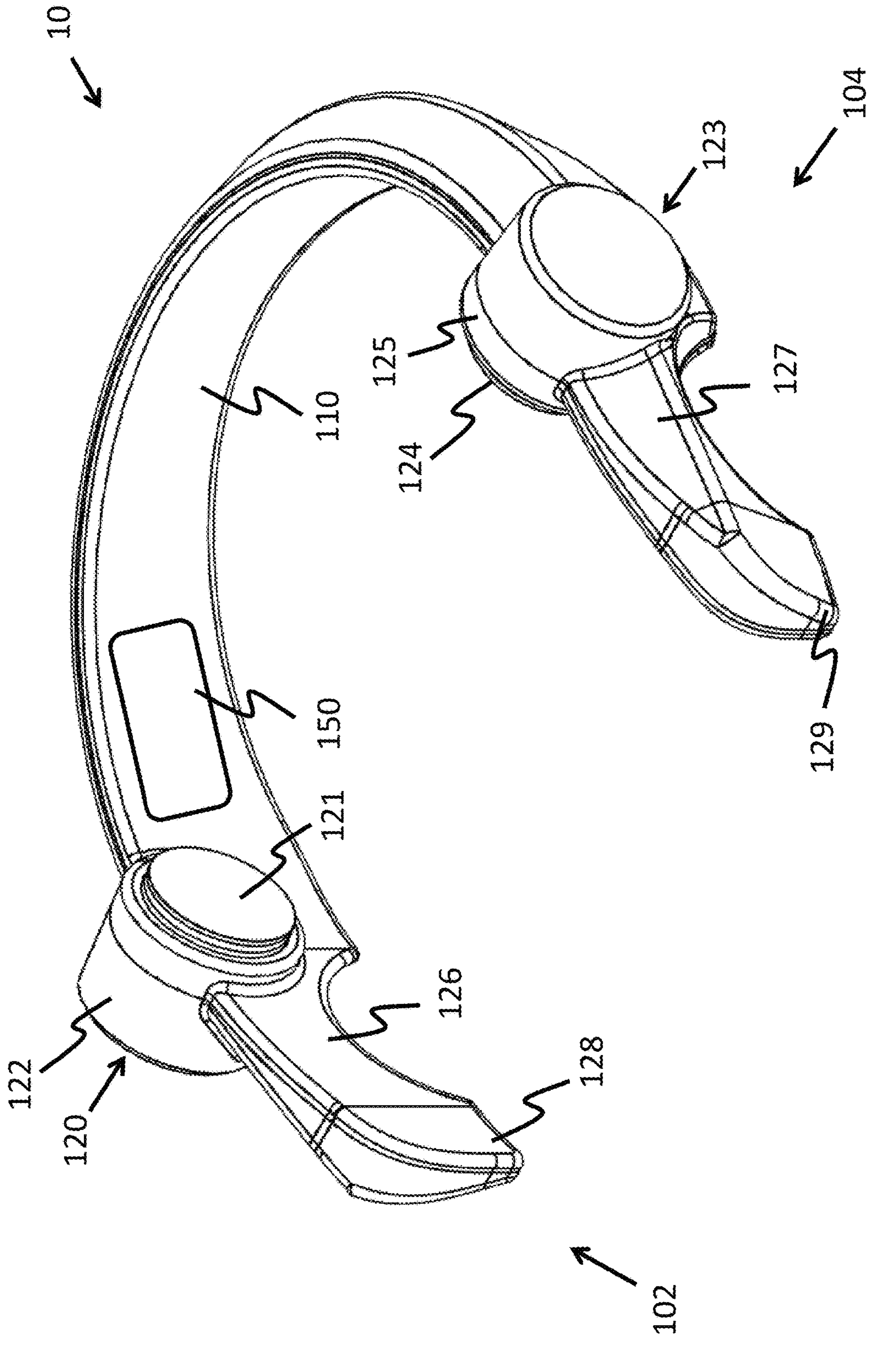
FIG. 1 is a perspective view of an apparatus for treating tinnitus in accordance with the present disclosure.

While the making and using of various embodiments of the present disclosure are discussed in detail herein, it should be appreciated that the present disclosure provides many applicable inventive concepts that are embodied in a wide variety of specific contexts. The specific embodiments discussed herein are merely illustrative of specific ways to make and use the disclosure and do not delimit the scope of the disclosure. Those of ordinary skill in the art will recognize numerous equivalents to the specific apparatuses, systems, and methods described herein. Such equivalents are considered to be within the scope of this disclosure and may be covered by the claims.

Furthermore, the described features, structures, or characteristics of the disclosure may be combined in any suitable manner in one or more embodiments. In the description contained herein, numerous specific details are provided, such as examples of programming, software, user selections, hardware, hardware circuits, hardware chips, or the like, to provide understanding of embodiments of the disclosure. One skilled in the relevant art will recognize, however, that the disclosure may be practiced without one or more of the specific details, or with other methods, components, materials, apparatuses, devices, systems, and so forth. In other instances, well-known structures, materials, or operations may not be shown or described in detail to avoid obscuring aspects of the disclosure.

The aforementioned features and advantages of the embodiments will become more fully apparent from the description and appended claims, or may be learned by the practice of embodiments as set forth herein. As will be appreciated by one skilled in the art, aspects of the present disclosure may be embodied as an apparatus, system, method, computer program product, or the like. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module," or "system." Furthermore, aspects of the present disclosure may take the form of a computer program product embodied in one or more computer-readable media having program code embodied thereon.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

The words "connected", "attached", "joined", "mounted", "fastened", and the like should be interpreted to mean any manner of joining two objects including, but not limited to, the use of any fasteners such as screws, nuts and bolts, bolts, pin and clevis, and the like allowing for a stationary, translatable, or pivotable relationship; welding of any kind such as traditional MIG welding, TIG welding, friction welding, brazing, soldering, ultrasonic welding, torch welding, inductive welding, and the like; using any resin, glue, epoxy, and the like; being integrally formed as a single part together; any mechanical fit such as a friction fit, interference fit, slidable fit, rotatable fit, pivotable fit, and the like; any combination thereof; and the like.

Referring generally to the Figures, a headset apparatus (apparatus) 10 for treating tinnitus (e.g., a tinnitus treatment device) is shown, according to various embodiments of the present disclosure. In some embodiments, the apparatus 10 is configured to treat tinnitus (in order to prevent recurrence of tinnitus) using low frequency tones. In other embodiments, the apparatus 10 is configured to mask tinnitus (in order to lessen the symptoms and/or effects of tinnitus) using high frequency tones. In other embodiments still, the apparatus 10 is configured to both treat tinnitus using low frequency tones, as well as mask tinnitus using high frequency tones. In other words, the low frequency tones may be produced to the exclusion of the high frequency tones and vice-versa, or both the low and high frequency tones may be produced by the apparatus 10 simultaneously, depending on the implementation. In some embodiments, the apparatus 10 performs various methods and functions as an individual unit. In other embodiments, the apparatus 10 functions in accordance with other components in a system.

Referring to FIGS. 1-9, the apparatus 10 is shown as configured to treat tinnitus using low frequency tones, according to some embodiments of the present disclosure. Generally, the apparatus 10 may be a small personal electronic wearable device that provides immediate treatment and/or rehabilitation from a condition of tinnitus. The apparatus 10 may include a semi-circular strap 110 that joins a first side 102 (terminating in a first tip 128) of the apparatus 10 with a second side 104 (terminating in a second tip 129) of the apparatus 10. The apparatus 10 may treat tinnitus by transmitting a low frequency vibration via one or more bone conductors (e.g., bone conducting devices, bone oscillators, bone conducting transducers, etc.). For example, the apparatus 10 may further include a first low frequency bone conductor 120 located on the first side 102 between the first tip 128 and the semi-circular strap 110, a second low frequency bone conductor 123 located on the second side 104 between the second tip 129 and the semi-circular strap 110, and a controller 150. As described in greater detail below with reference to FIGS. 8A-9, the apparatus 10 may, using the semi-circular strap 110, place the first and second low frequency bone conductors 120, 123 against the post auricular mastoid bone (e.g., a right mastoid bone 18 as depicted therein) in order to provide treatment of tinnitus.

In some embodiments, the controller 150 is housed within the material of the apparatus 10 as shown. In other embodiments, the controller 150 may be located externally to the apparatus 10, as shown with reference to FIG. 29. Depending on the implementation of the present disclosure, some or all functions of the components of the apparatus 10 are controlled by the controller 150. For example, the controller 150 may control the first and second low frequency bone conductors 120, 123. The controller 150 is described in greater detail below with reference to FIG. 28.

Figure 8A:
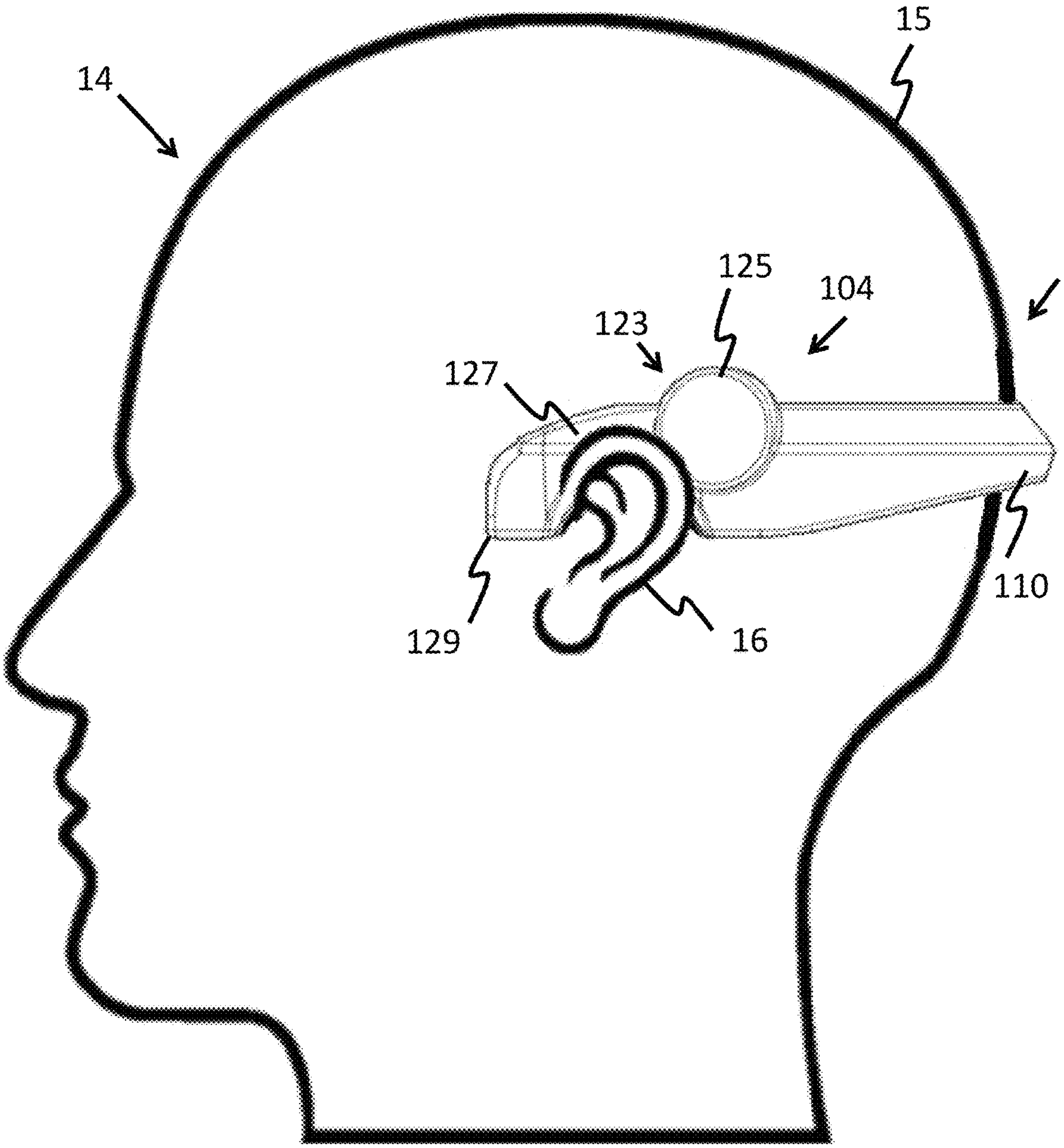
FIG. 8A is a side view of the apparatus of FIG. 1 positioned on a head of a user in accordance with the present disclosure.
Figure 8B:
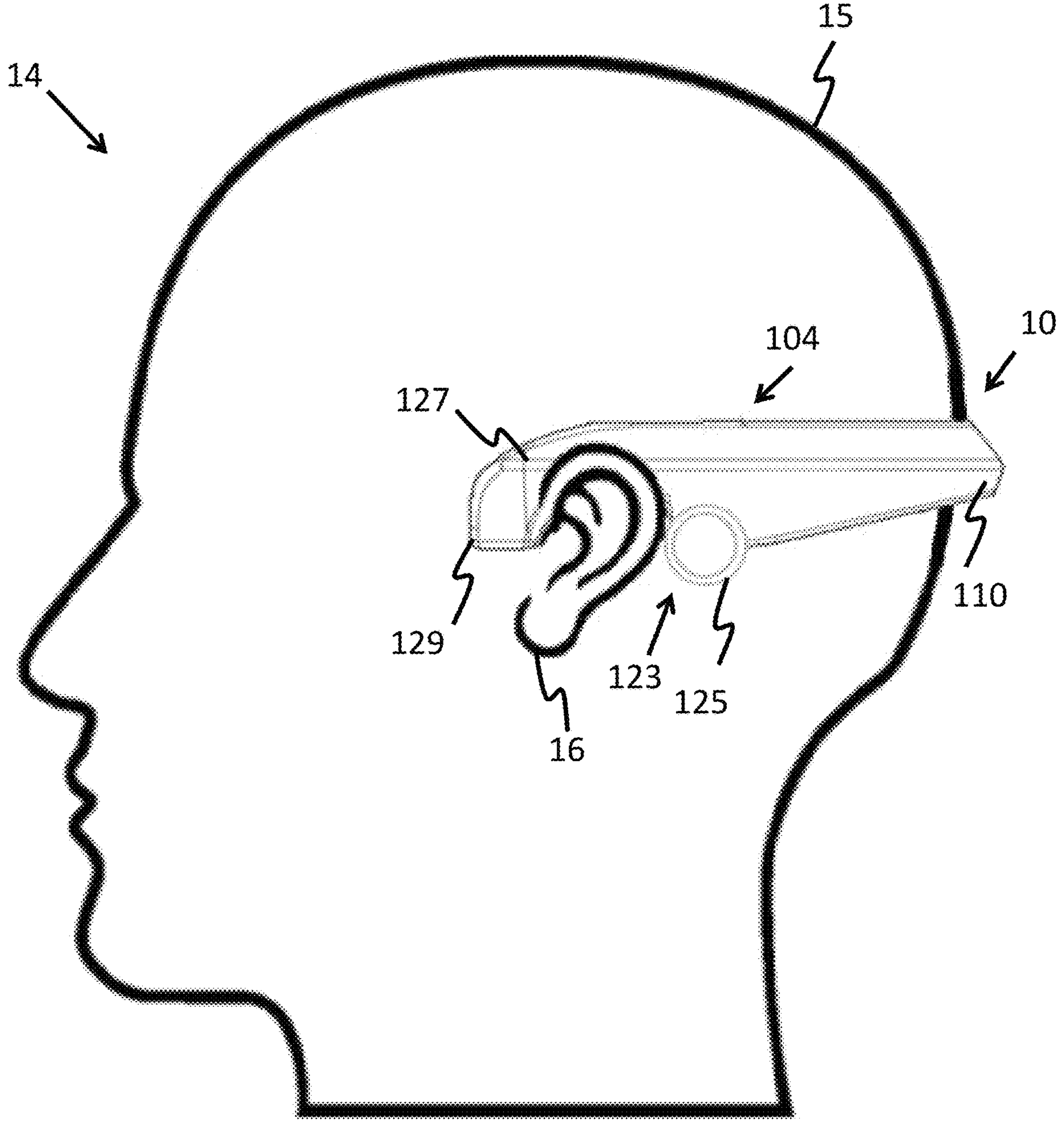
FIG. 8B is a side view of an alternative embodiment of the apparatus of FIG. 1 positioned on a head of a user in accordance with the present disclosure.
Figure 9:
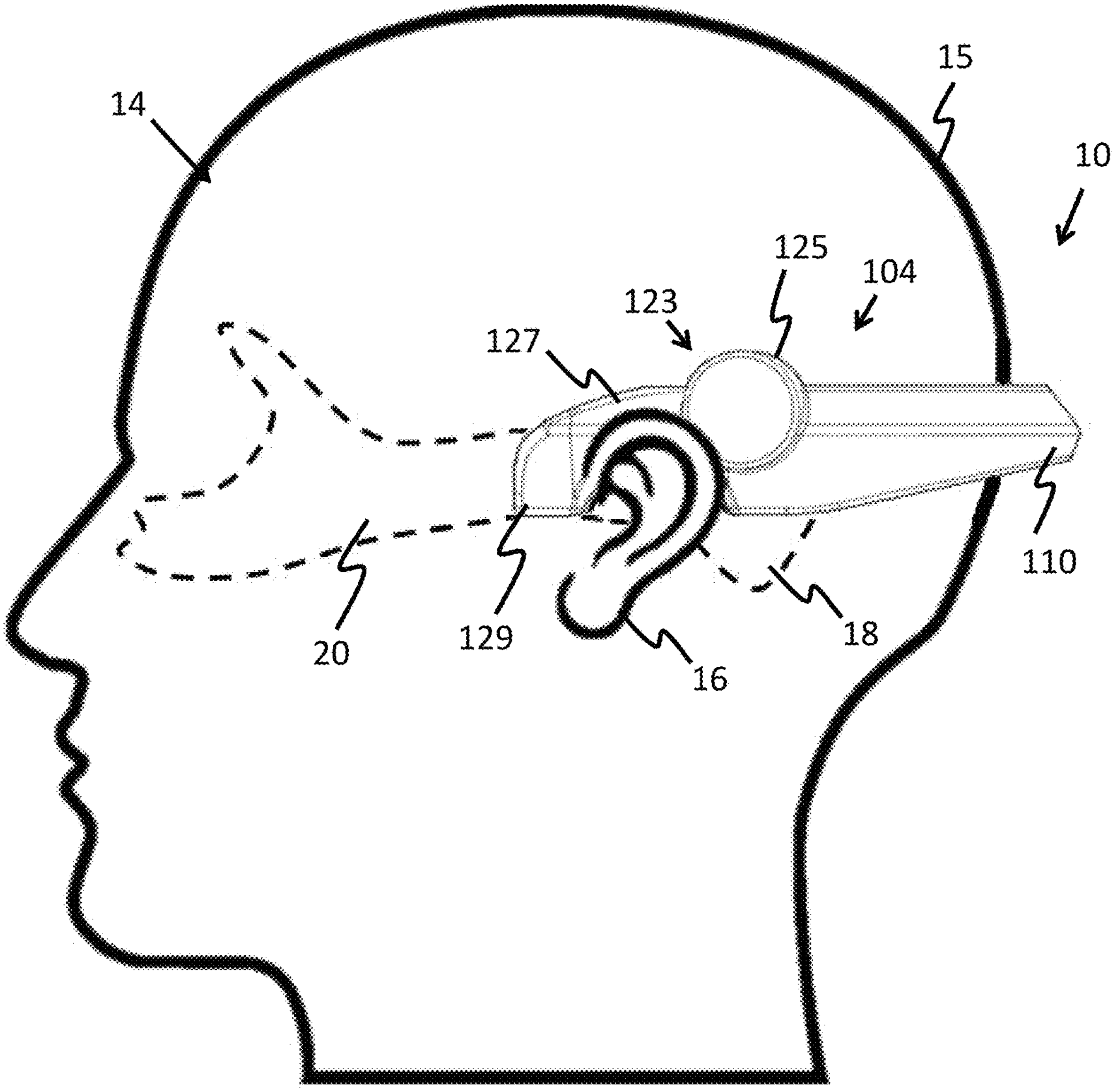
FIG. 9 is a side view of the apparatus of FIG. 1 positioned on a head of a user in accordance with the present disclosure.

In some embodiments, the first and second low frequency bone conductors 120, 123 are electromechanical oscillation devices configured to produce vibrotactile bone conduction for a user 14 (depicted with reference to FIGS. 8A-9. 11A-12, and 19-20). Generally, bone conduction is the conduction of sound to the inner ear primarily through the bones of the skull (e.g., bones within a head 15 of the user 14). As discussed in greater detail below, by retaining the various bone conductors discussed herein against the head 15 of the user 14 with a slight amount of pressure and producing vibrations, such vibrations propagate sound waves that vibrate particular bones in the head of the user 14, which may allow the user 14 to perceive audio content without blocking the ear canal. In other words, such vibrations may be perceived as a vibrotactile sensation rather than being perceived via the hearing and/or auditory pathways of the head 15 of the user 14. Advantageously, bone conduction as described herein, performed at particular patterns of frequency and volume (e.g., "programmed sessions," "treatment sessions," etc.) may allow for treatment of tinnitus.

In some embodiments, the first and second low frequency bone conductors 120, 123 are configured to produce tones of between fifty and one-hundred-and-ten hertz. In other embodiments, the first and second low frequency bone conductors 120, 123 are configured to produce tones of a different range (e.g., between forty and seventy hertz, between thirty and eighty hertz, between ten and one-hundred-and-fifty hertz, etc.). In general, the tone produced by the first and second low frequency bone conductors 120, 123 may be of any frequency at or less than four-hundred hertz in order to facilitate treatment of tinnitus in the user 14.

In some embodiments, the first and second low frequency bone conductors 120, 123 are configured to produce tones at a particular volume in order for the tones to be perceivable by the user 14 by a narrow margin. For example, the first and second low frequency bone conductors 120, 123 may produce tones at about forty decibels. As another example, a first auditory threshold for the user 14 may be determined (as discussed below with reference to FIG. 35) for the low frequency tones administered by the first and second bone conductors 120, 123, and the first and second bone conductors 120, 123 may be set at a volume that is marginally above the first auditory threshold value. For example, the first auditory threshold value may be the volume for low frequency tones at which, at any greater volume, the user 14 is able to perceive the tones, and at any lesser volume, the user 14 is not able to perceive the tones. In turn, the volume for the first and second low frequency bone conductors 120, 123 may be set at a volume that is about five to ten decibels above the first auditory threshold.

Figure 2:
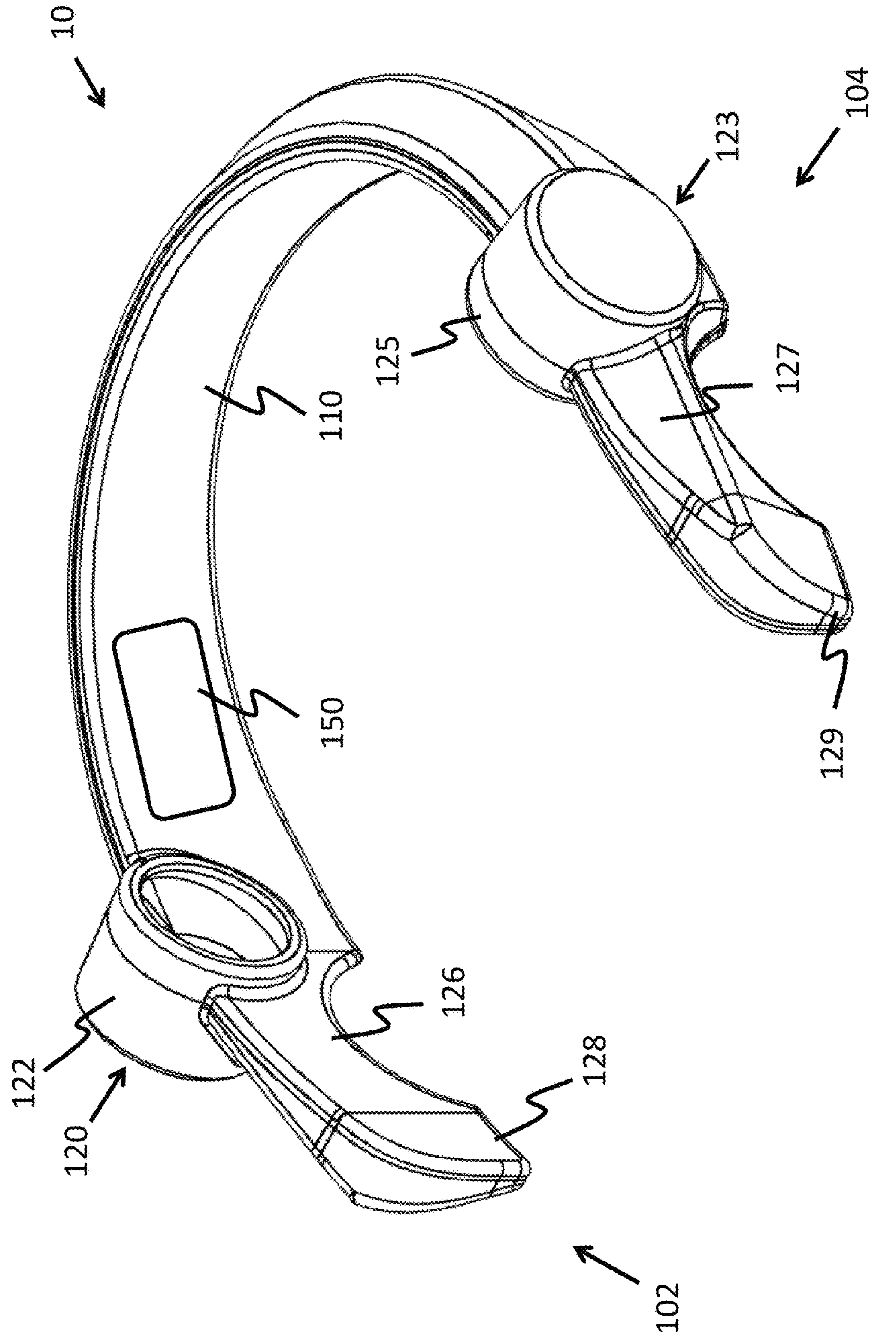
FIG. 2 is a perspective view of the apparatus of FIG. 1 in accordance with the present disclosure.
Figure 3:
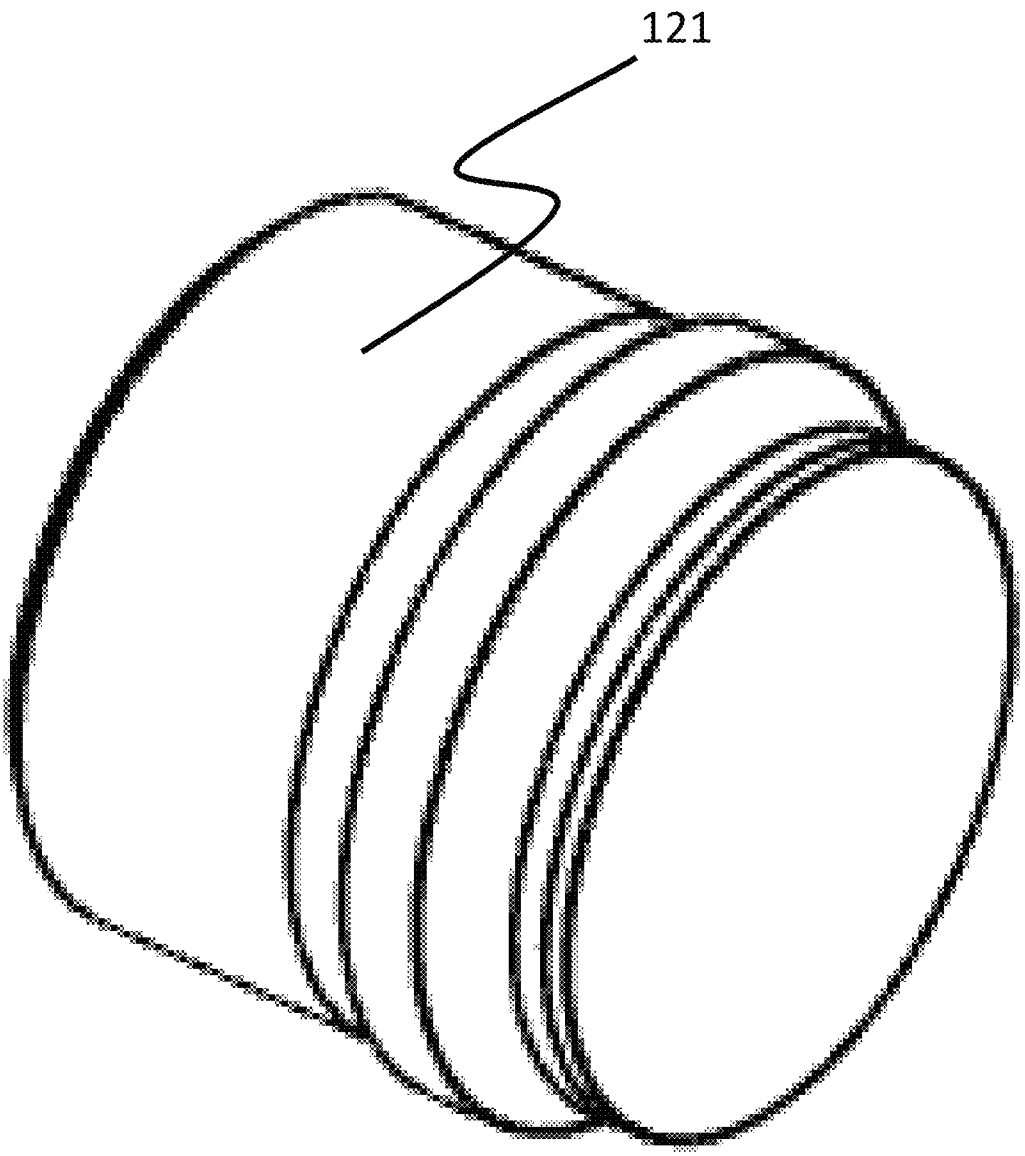
FIG. 3 is a perspective view of a bone conductor of the apparatus of FIG. 1 in accordance with the present disclosure.
Figure 4:
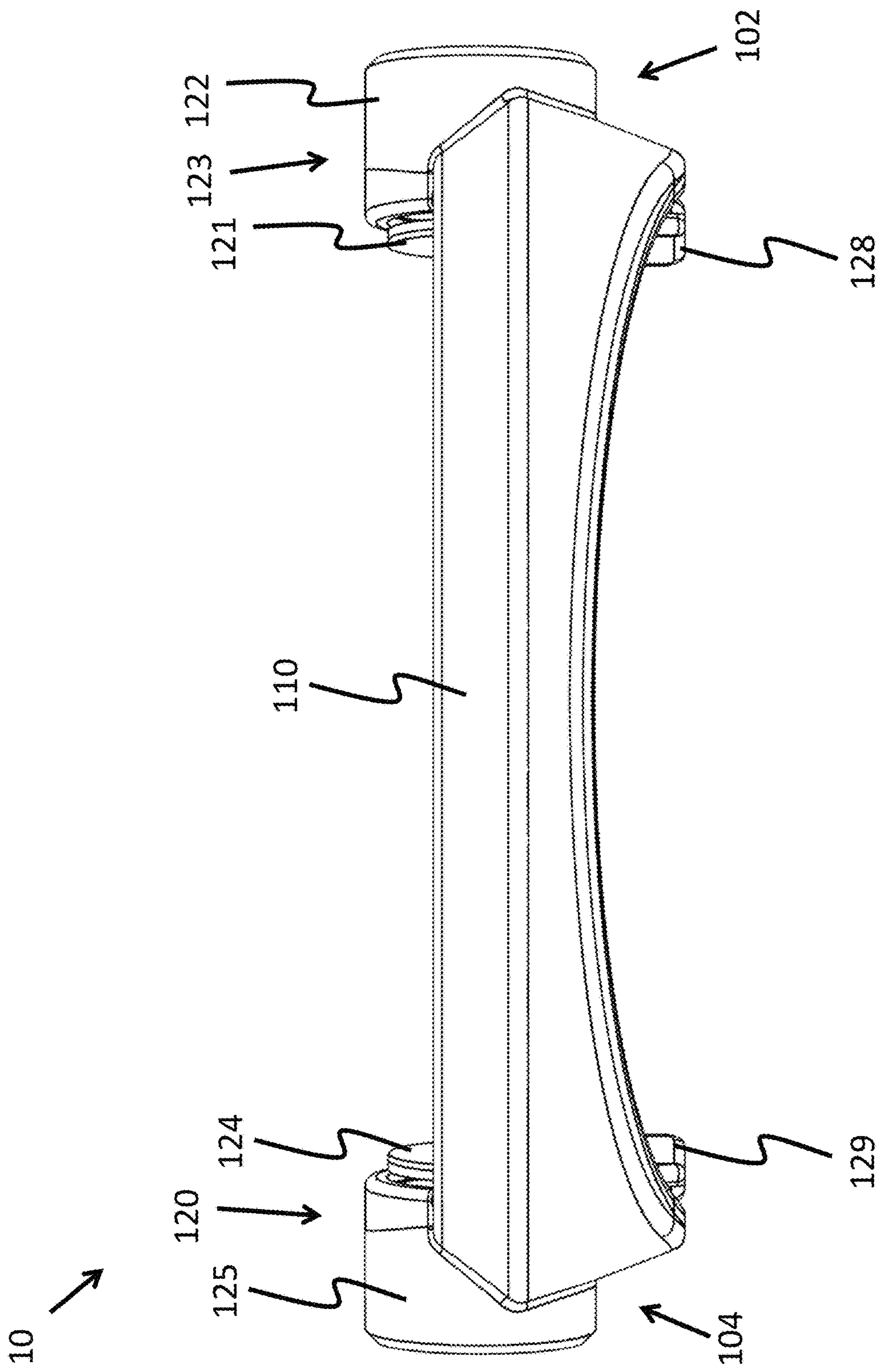
FIG. 4 is a rear view of the apparatus of FIG. 1 in accordance with the present disclosure.
Figure 5:
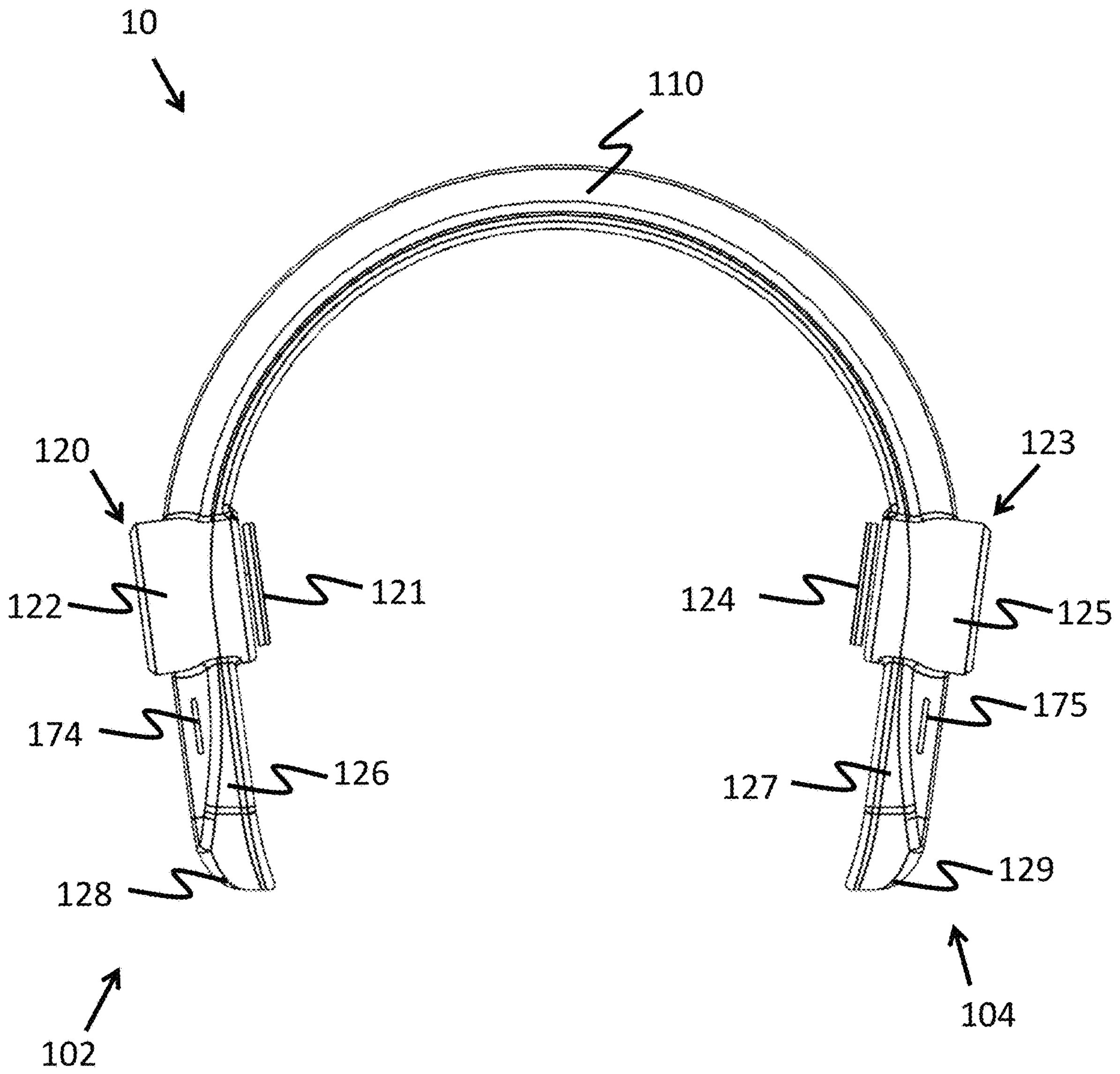
FIG. 5 is a top view of the apparatus of FIG. 1 in accordance with the present disclosure.

In some embodiments, the first low frequency bone conductor 120 includes a first transducer 121 (shown with particular reference to FIG. 3) retained within a first transducer housing 122 (shown with particular reference to FIG. 2). Similarly, the second low frequency bone conductor 123 may include a second transducer 124 retained within a second transducer housing 125. The first and second transducer housings 122, 125 may be large enough to retain the first and second transducers 121, 125, which may be approximately one inch in diameter, according to some embodiments. The first and second transducers 121, 124 may be bone conductors that convert electrical energy (e.g., electricity supplied by a power supply 142 discussed with reference to FIG. 28) to mechanical motion using an oscillating internal weight, thereby providing the aforementioned low-frequency tones to the user 14 in a vibrotactile fashion when the first and second low frequency bone conductors 120, 123 are applied to the head 15 of the user 14. In operation, for example (and as described in greater detail below with particular reference to FIGS. 8A-9), the surfaces of the first and second transducers 121, 124 that protrude from the first and second transducer housings 122, 124 (respectively) may make contact with the skin of the user 14 in order to transmit vibrations to the bone underneath. Depending on the implementation of the present disclosure, the first and second transducer devices 121, 124 may simply be off-the-shelf bone conductor products. In other embodiments, the first and second transducer devices 121, 124 may be custom-made in order to perform the systems and methods discussed herein.

Referring particularly to FIGS. 8A-9, the apparatus 10 is shown secured on the head 15 of the user 14, according to some embodiments of the present disclosure. As mentioned above, the apparatus 10 may include the semi-circular strap 110. As shown, the semi-circular strap 110 may be configured to be positioned about a rear portion of the head 15 of the user 14. In some embodiments, the semi-circular strap 110 is rigid. In other embodiments, the semi-circular strap 110 is at least partially flexible such that the semi-circular strap 110 is operable to adjust to the shape of the rear portion of the head 15 of the user 14 and hold the first and second low frequency bone conductors 120, 123 (due to mild pressure facilitated by the semi-circular strap 110, for example) in contact with the head 15 of the user 14 in order to facilitate vibrotactile bone conduction. Accordingly, the semi-circular strap 110 may be constructed of any suitable material including, but not limited to, rubber, plastic, etc. In some embodiments, the apparatus 10 includes a first over-ear strap 126 on the first side 102 and a second over-ear strap 127 on the second side 104. Each of the first and second over-ear straps 126, 127 may be configured to be positioned over a respective ear of the user 14. For example, the second over-ear strap 127 is shown to rest on a right ear 16 of the user 14. Each of the first and second over-ear straps 126, 127 may be rigid or at least partially flexible, similar to the semi-circular strap 110. The first and second over-ear straps 126, 127 then, may similarly be constructed of any suitable material including, but not limited to, rubber, plastic, etc.

As mentioned above, the first low frequency bone conductor 120 may be located on the first side 102 between the first tip 128 and the semi-circular strap 110, and the second low frequency bone conductor 123 may be located on the second side 104 between the second tip 129 and the semi-circular strap 110. In particular, and as shown here, the first low frequency bone conductor 120 may be located between the first over-ear strap 126 and the semi-circular strap 110, and the second low frequency bone conductor 123 may be located between the second over-ear strap 127 and the semi-circular strap 110.

In the implementation shown, each of the first and second low frequency bone conductors 120, 123 are configured to be positioned adjacent to and apply at least some pressure to one of the left or right auricular mastoid bones of the user 14. For example, as shown with particular reference to FIG. 9, the second low frequency bone conductor 123 is positioned over the right mastoid bone 18 of the user 14 (e.g., rearward of the right ear 16 of the user 14). Of course, one of skill in the art will understand that the left mastoid bone (not shown) is positioned on the opposite side of the head 15 of the user 14, and therefore the first low frequency bone conductor 120 may be positioned over the left mastoid bone of the user 14 (e.g., rearward of the left ear of the user 14). The low frequency tone is configured to be transmitted from each of the respective first and second low frequency bone conductors 120, 123 to the associated mastoid bone of the user 14 for treating tinnitus of the user 14 and preventing recurrence of the tinnitus following a treatment protocol. Such treatment protocols are described in greater detail below with reference to FIGS. 30-35.

As shown with particular reference to FIG. 8B, the second low frequency bone conductor 123 may be located near the bottom of the apparatus 10, and therefore be positioned directly behind the right ear 16 of the user 14. The first low frequency bone conductor 120 may be similarly positioned in such alternative embodiments. Advantageously, such a configuration may provide the first and second low frequency bone conductors 120, 123 directly over the left mastoid bone (not shown) and the right mastoid bone 18 of the user 14 (respectively), thereby improving the transmission of the low frequency tones generated by each of the first and second low frequency bone conductors 120, 123 to the left mastoid bone and the right mastoid bone 18 (respectively). It should be appreciated that the alternative embodiment shown with reference to FIG. 8B (in terms of the lower position of the first and second low frequency bone conductors 120, 123 relative to that which is depicted with reference to FIGS. 8A and 9) may be similarly applied to any of the embodiments of the apparatus 10 depicted herein.

Figure 10:
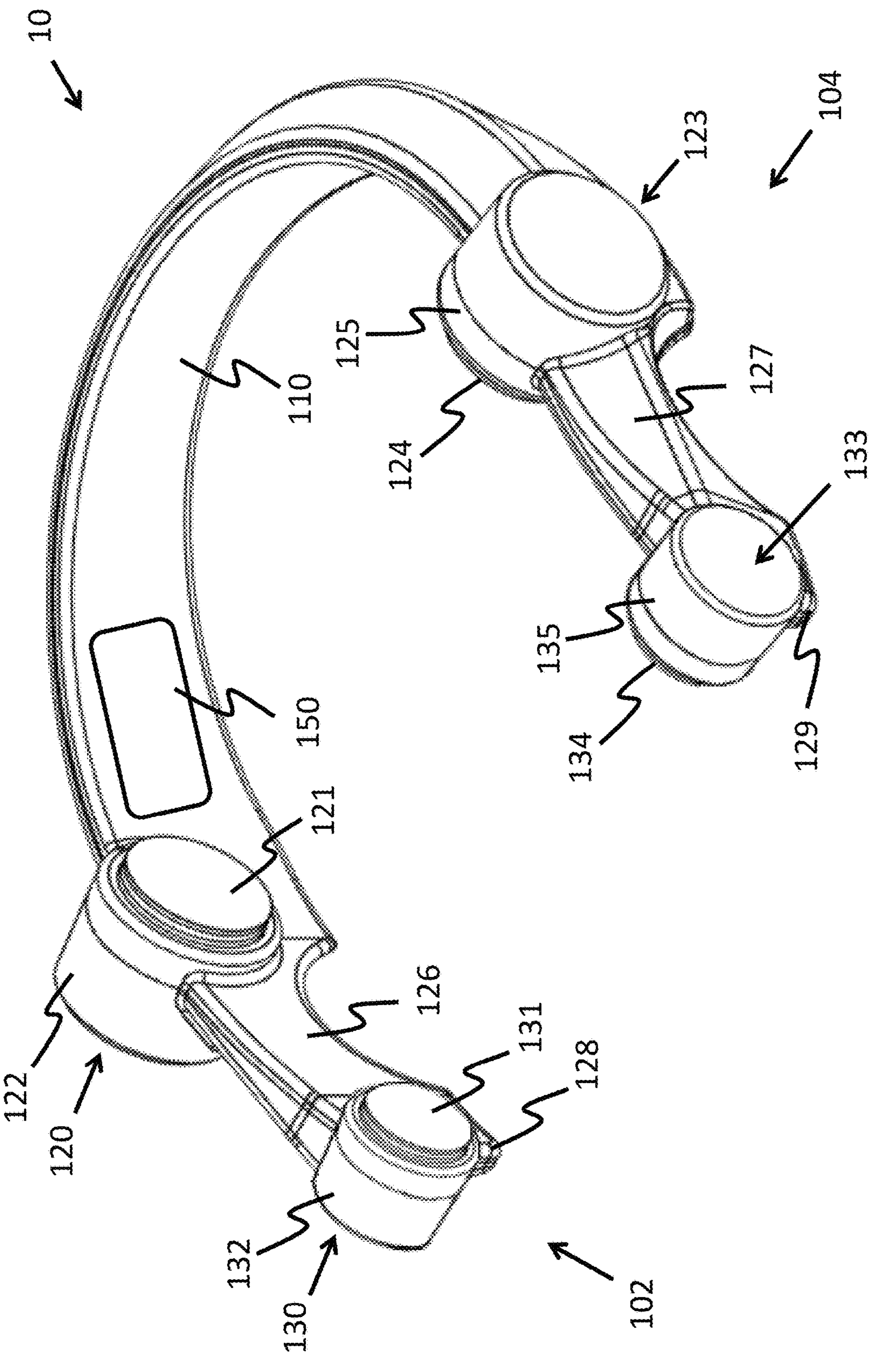
FIG. 10 is a perspective view of an apparatus for treating tinnitus in accordance with the present disclosure.
Figure 11A:
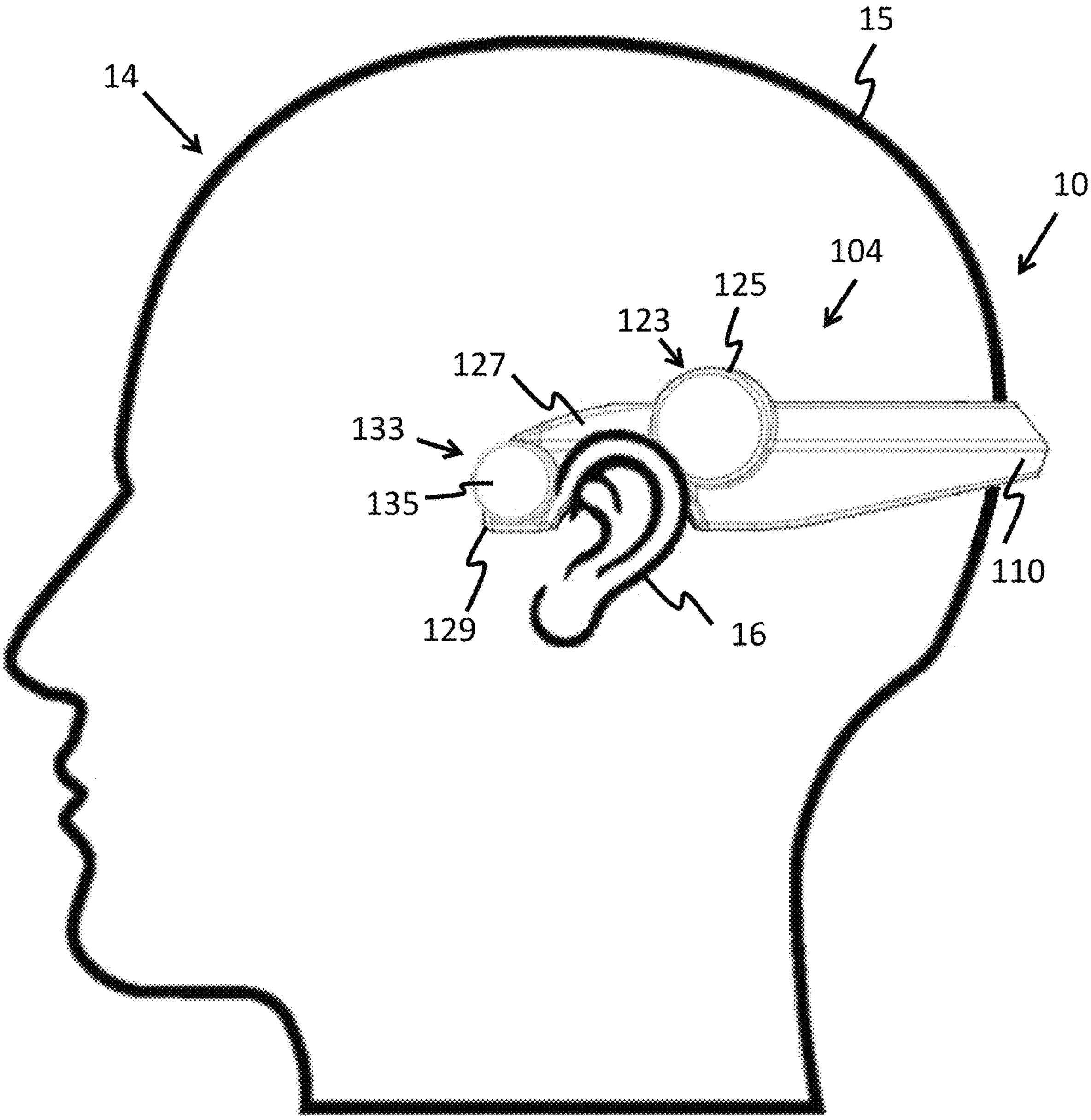
FIG. 11A is a side view of the apparatus of FIG. 10 positioned on a head of a user in accordance with the present disclosure.
Figure 11B:
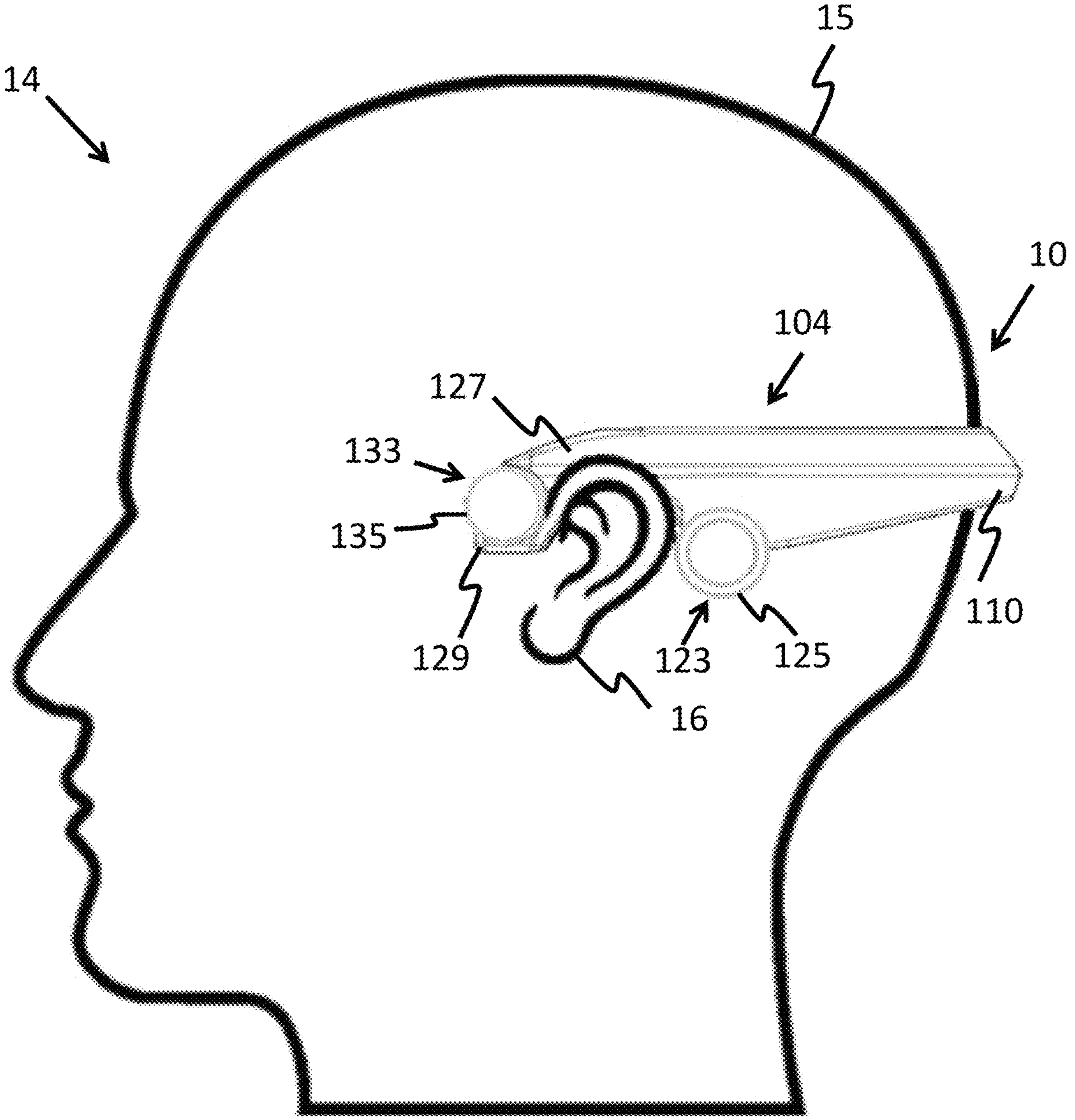
FIG. 11B is a side view of an alternative embodiment the apparatus of FIG. 10 positioned on a head of a user in accordance with the present disclosure.
Figure 12:
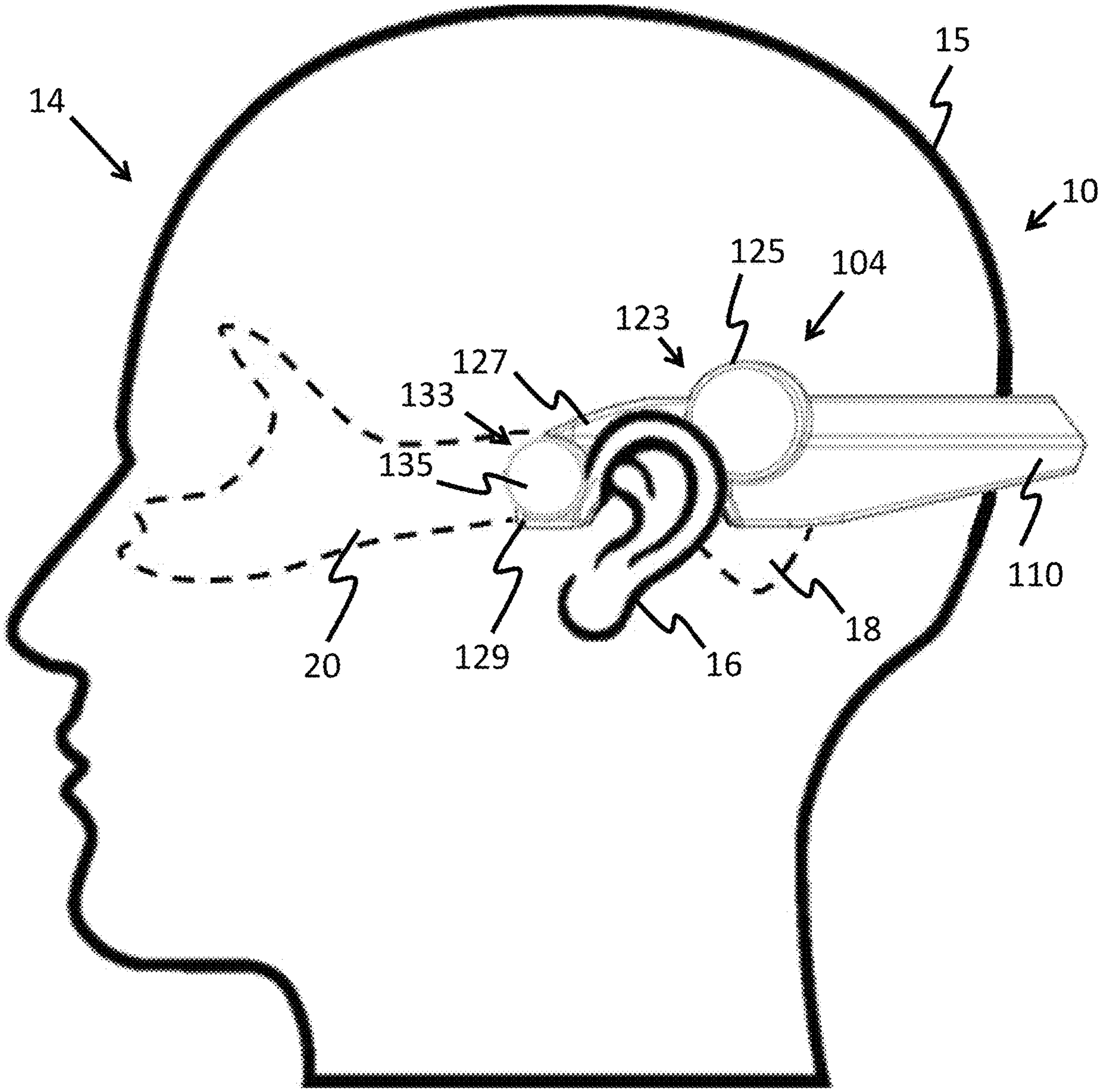
FIG. 12 is a side view of the apparatus of FIG. 10 positioned on a head of a user in accordance with the present disclosure.
Figure 13:
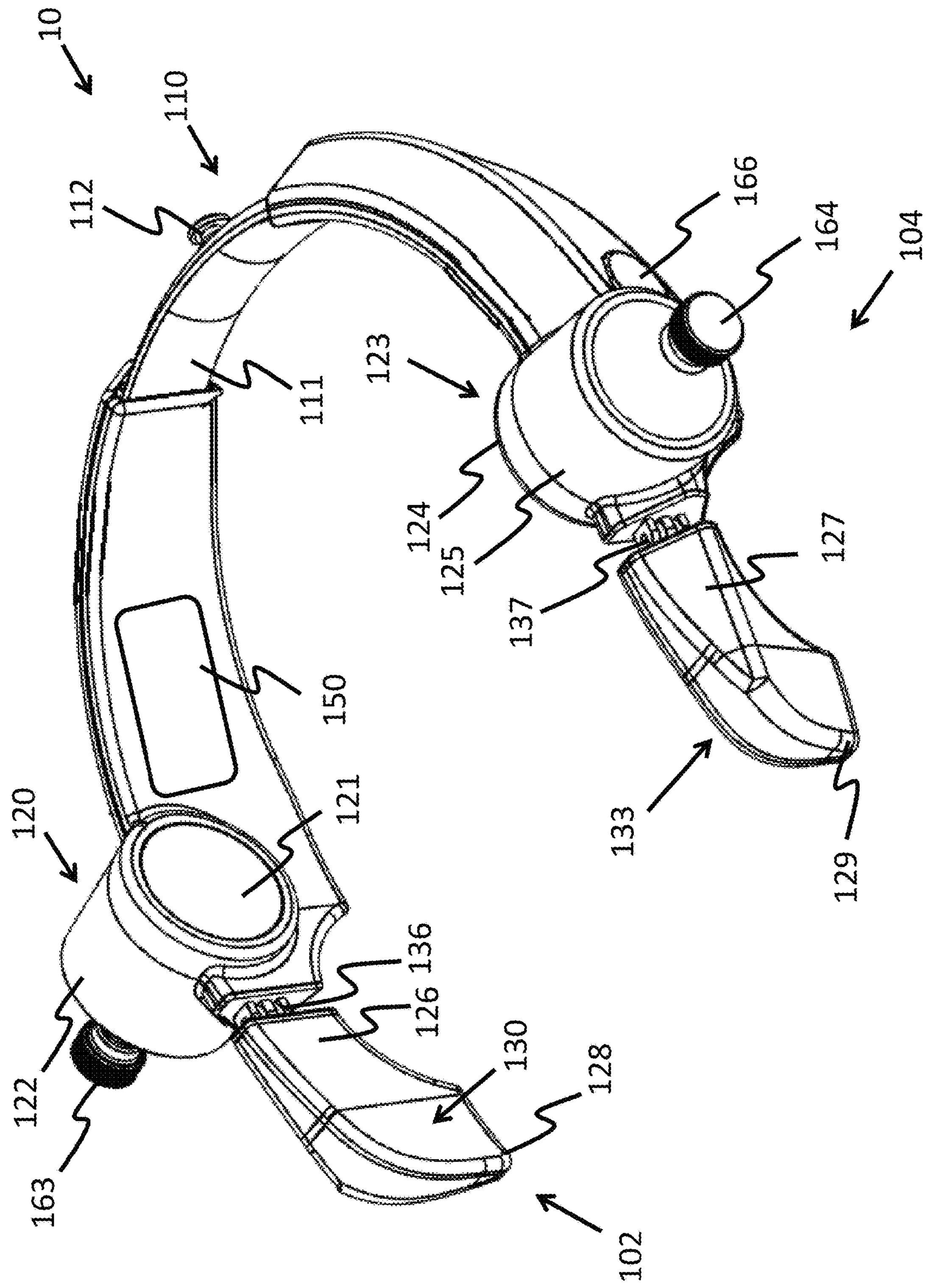
FIG. 13 is a perspective view of an apparatus for treating tinnitus in accordance with the present disclosure.
Figure 14:
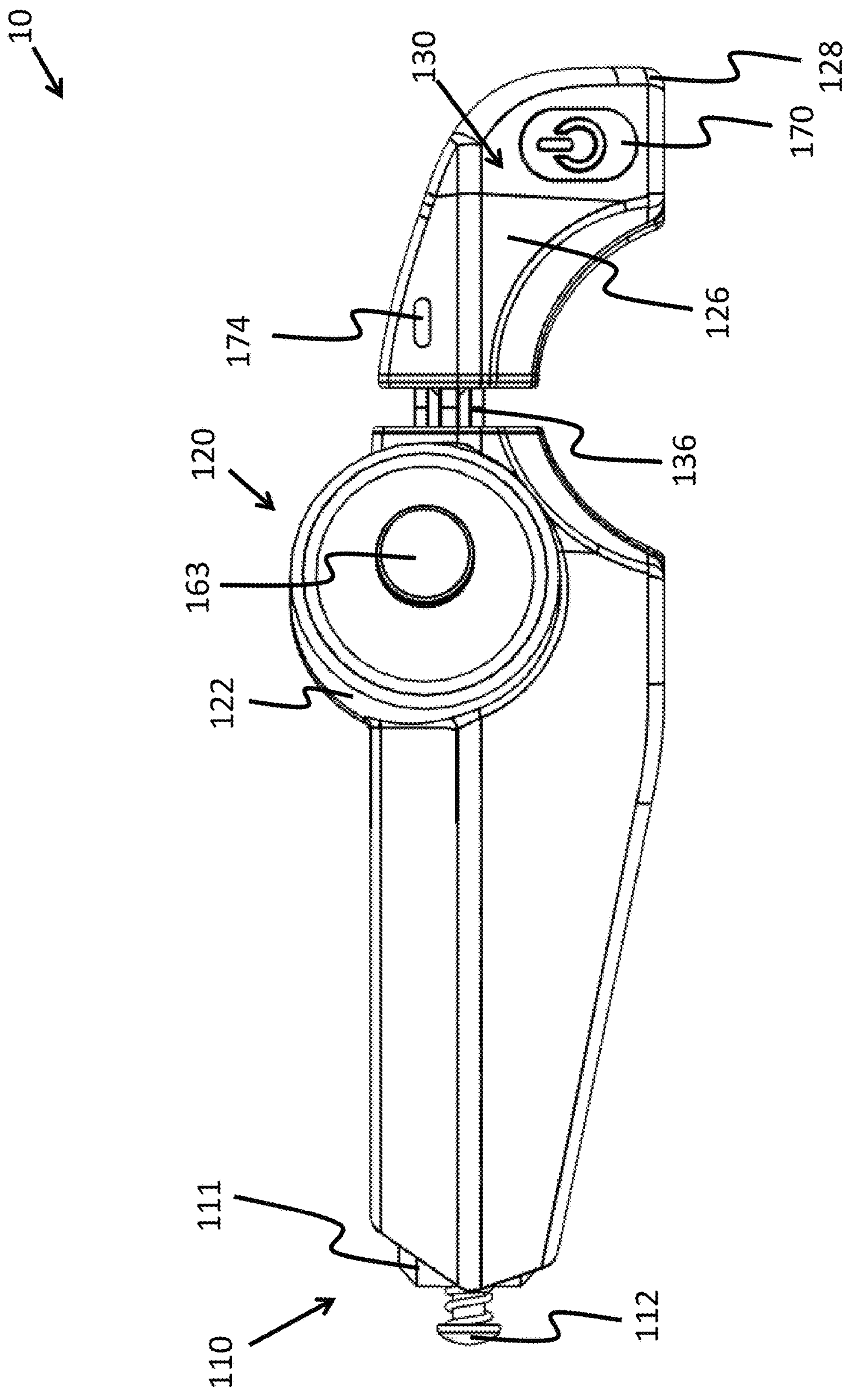
FIG. 14 is a side view of the apparatus of FIG. 13 in accordance with the present disclosure.
Figure 15:
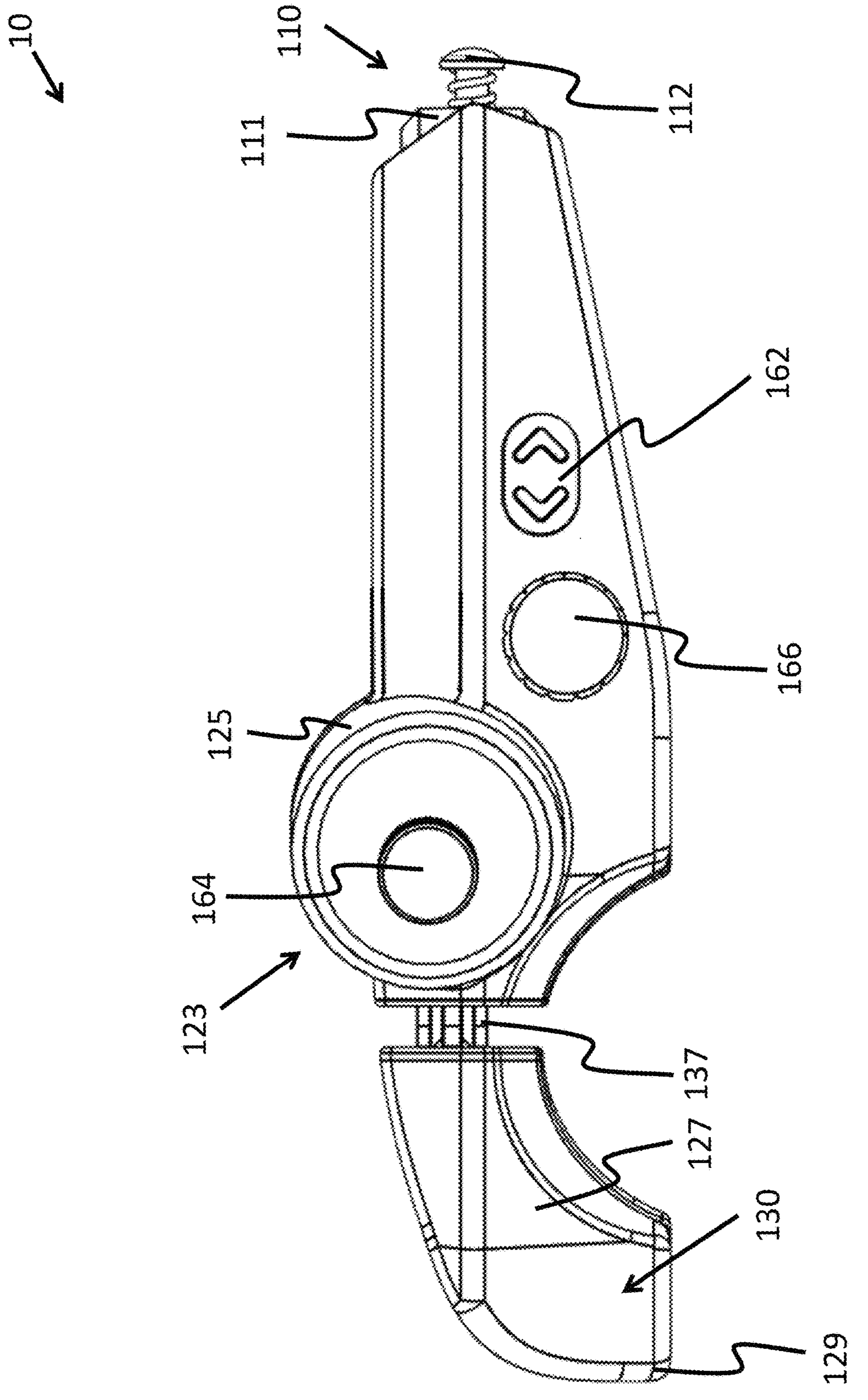
FIG. 15 is a side view of the apparatus of FIG. 13 in accordance with the present disclosure.
Figure 16:
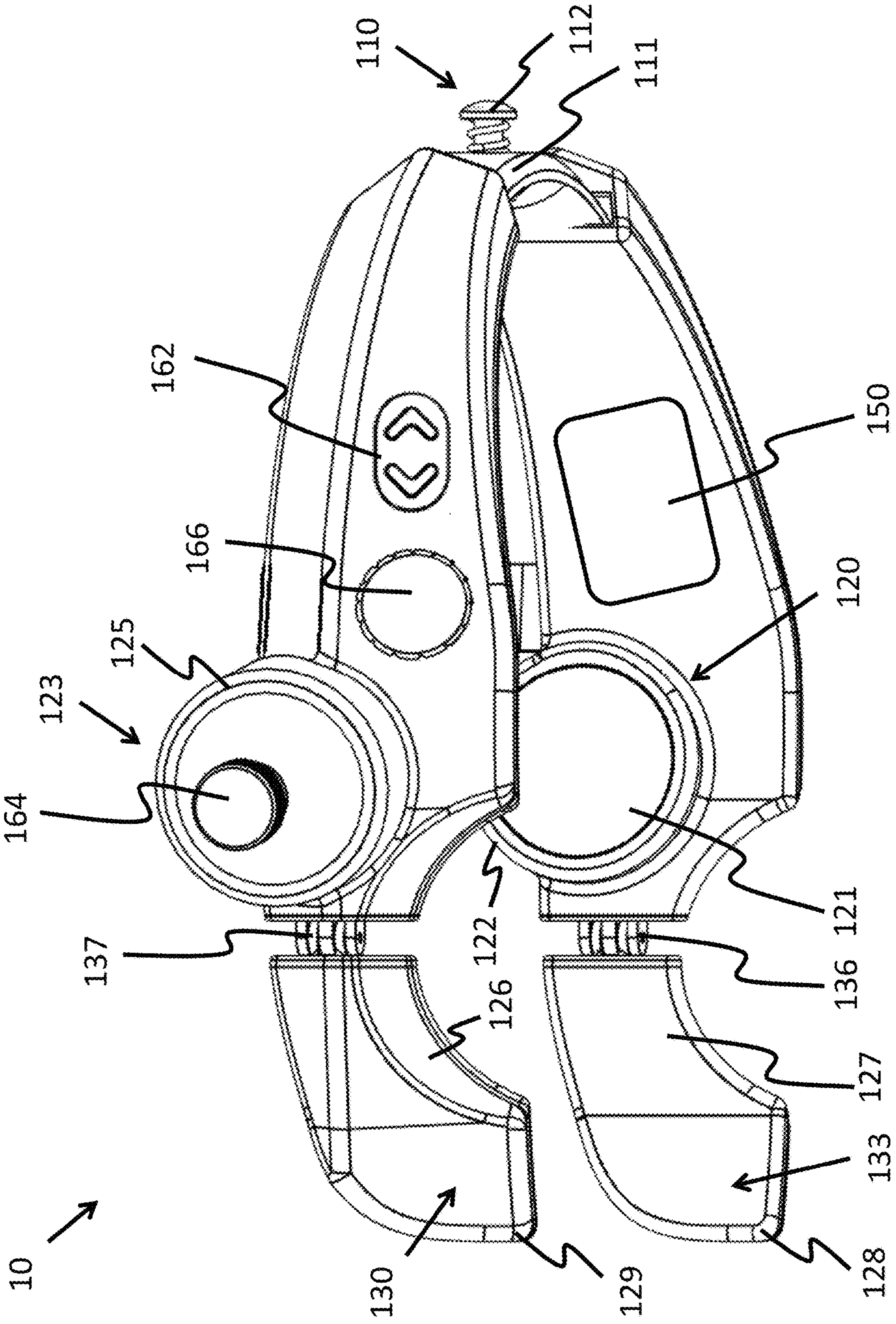
FIG. 16 is a side perspective view of the apparatus of FIG. 13 in accordance with the present disclosure.
Figure 17:
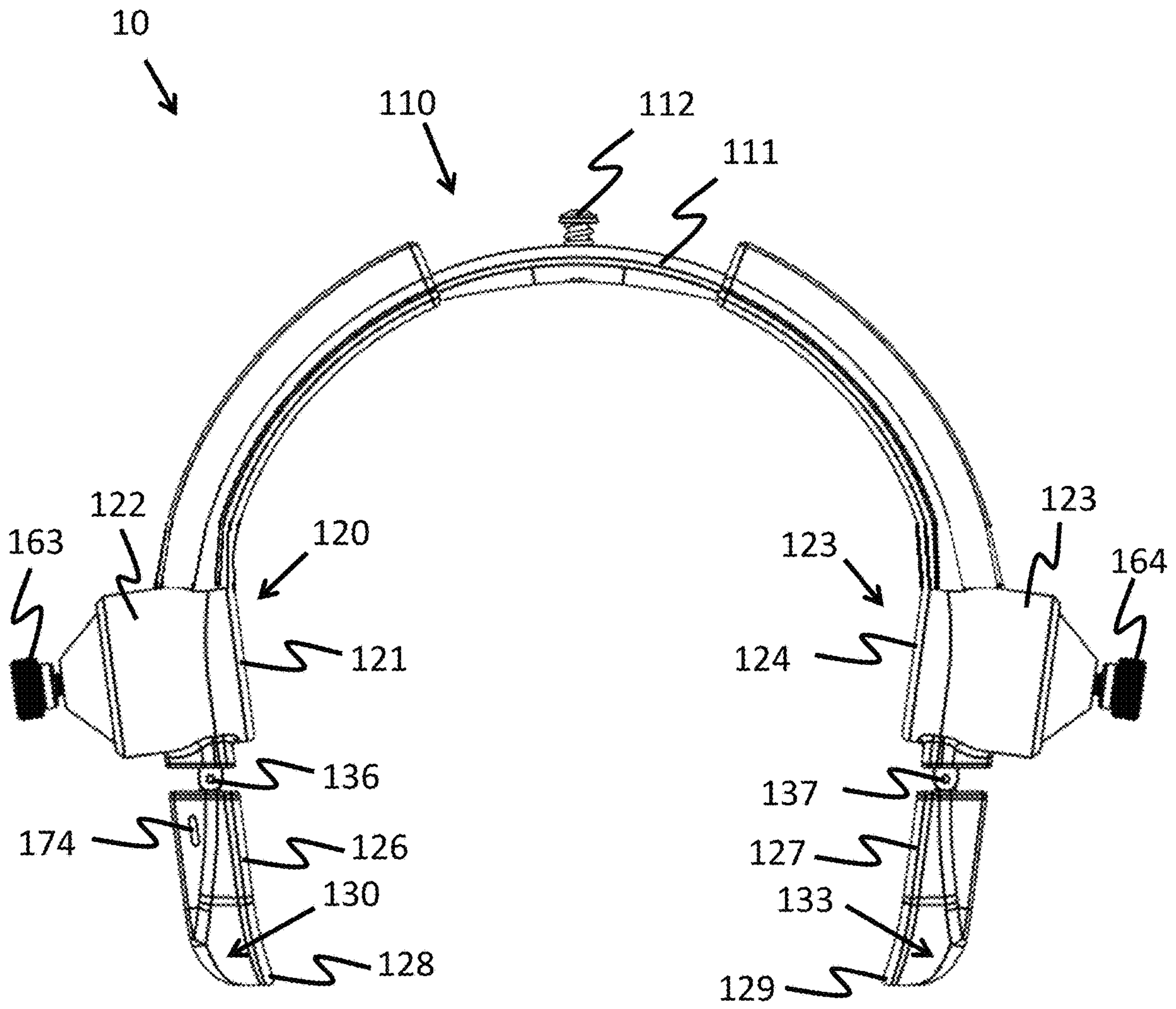
FIG. 17 is a top view of the apparatus of FIG. 13 in accordance with the present disclosure.
Figure 18:
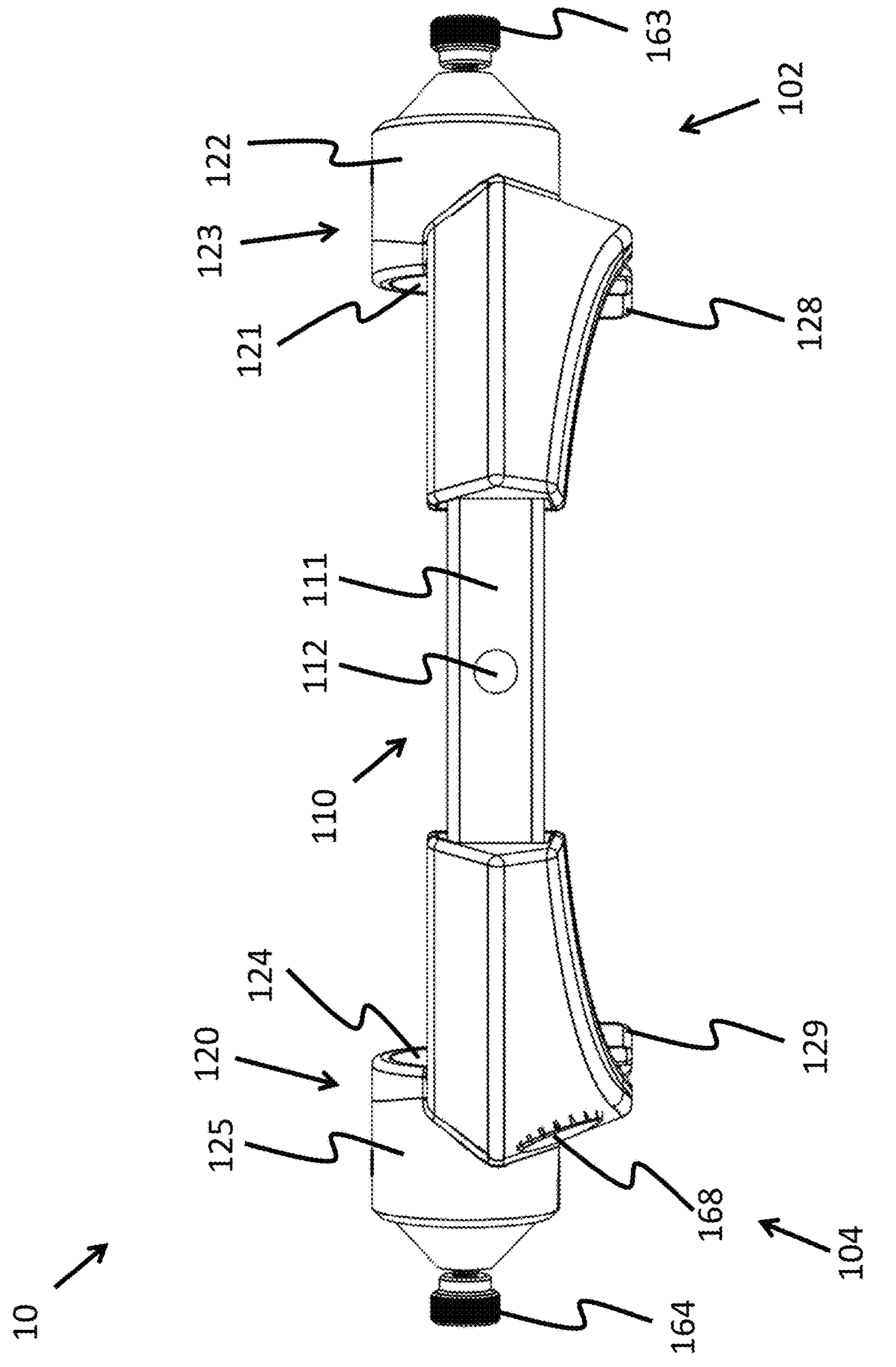
FIG. 18 is a rear view of the apparatus of FIG. 13 in accordance with the present disclosure.
Figure 19:
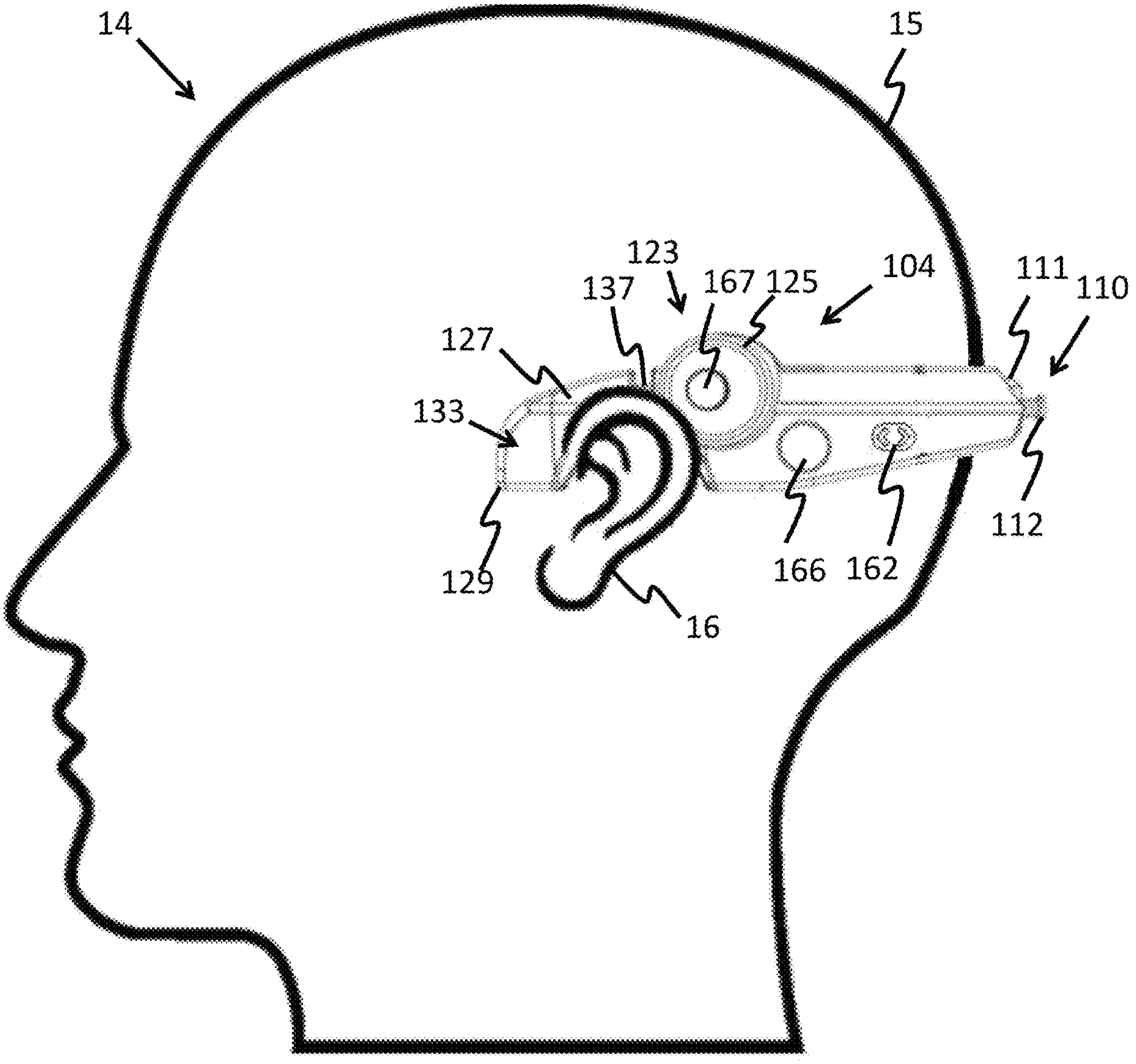
FIG. 19 is a side view of the apparatus of FIG. 13 positioned on a head of a user in accordance with the present disclosure.

Referring to FIGS. 10-12, the apparatus 10 is shown as configured to treat tinnitus using low frequency tones (as discussed above), as well as mask tinnitus using high frequency tones, according to some embodiments of the present disclosure. Referring particularly to FIG. 10, the apparatus 10 may include some or all of the components of the apparatus 10 as discussed above with reference to FIGS. 1-9 (e.g., the apparatus 10 as configured for solely treating tinnitus using low frequency tones). However, in order to additionally provide masking of tinnitus, the apparatus 10 further transmit a high frequency vibration via one or more bone conductors. For example, the apparatus 10 may further include a first high frequency bone conductor (e.g., a high frequency oscillator device) 130 located on the first side 102 at or near the first tip 128 and a second high frequency bone conductor 133 located on the second side 104 at or near the second tip 129. Similar to the first and second low frequency bone conductors 120, 123, the first and second high frequency bone conductors 130, 133 may be electromechanical devices configured to produce vibrotactile bone conduction for the user 14. In some embodiments, the first high frequency bone conductor 130 is located on a side of the first over-ear strap 126 opposite the first low frequency bone conductor 120. Similarly, the second high frequency bone conductor 133 may be located on a side of the second over-ear strap 127 opposite the second low frequency device 123. As described in greater detail below with reference to FIGS. 11A-12 and 19-20, the apparatus 10 may, using the semi-circular strap 110 (and, depending on the implementation other components of the apparatus 10) place the first and second high frequency bone conductors 130, 133 against the pre-auricular zygomatic process (e.g., a right zygomatic bone 20 depicted therein) in order to providing masking of tinnitus.

In some embodiments, the first and second high frequency bone conductors 130, 133 are constructed in a similar fashion as the first and second low frequency bone conductors 120, 123, while configured to provide tones of a higher frequency than the first and second low frequency devices 120, 123. Accordingly, the first and second high frequency devices 130, 133 may be electromechanical devices configured to produce high-frequency tones by converting electrical energy to mechanical motion using an oscillating internal weight, thereby providing high-frequency tones to the user 14 in a vibrotactile fashion. The first and second high-frequency devices 130, 133 may be configured to produce tones of between six-thousand and ten-thousand hertz. In other embodiments, the first and second high frequency bone conductors 130, 133 are configured to produce tones of a different range (e.g., between five-thousand and twelve-thousand hertz, between four-thousand and fourteen-thousand hertz, etc.). In general, the tone produced by the first and second high frequency bone conductors 130, 133 may be of any frequency between three-thousand and twenty-five-thousand hertz. As compared to the tones provided by the first and second low frequency bone conductors 120, 123 (e.g., tones configured for perception by the user 14, which may be configured for treatment of tinnitus), the tones provided by the first and second high frequency bone conductors 130, 133 may rather be understood as masking noise or sound (e.g., white noise, pink noise, violet noise, brown noise, etc.) that masks tinnitus symptoms of the user 14.

In some embodiments, and similar to the first and second low frequency bone conductors 120, 123, the first and second high frequency bone conductors 130, 133 are configured to produce tones at a particular volume in order for the tones to be perceivable by the user 14 by a narrow margin (e.g., at about forty decibels). In addition to the first auditory threshold associated with the first and second low frequency bone conductors 120, 123, a second auditory threshold for the user 14 may be determined for the high frequency tones administered by the first and second high frequency bone conductors 130, 133, and the first and second high frequency bone conductors 130, 133 may be set at a volume that is marginally above the second auditory threshold value. For example, the second auditory threshold value may be the volume for high frequency tones at which, at any greater volume, the user 14 is able to perceive the tones, and at any lesser volume, the user 14 is not able to perceive the tones. In turn, the volume for the first and second high frequency bone conductors 130, 133 may be set at a volume that is about five to ten decibels above the second auditory threshold.

As mentioned above, the first and second high frequency bone conductors 130, 133 may be constructed in a similar fashion as the first and second low frequency bone conductors 120, 123. Accordingly, the first high frequency bone conductor 130 may include a third transducer 131 retained within a third transducer housing 132, and the second high frequency bone conductor 133 may include a fourth transducer 134 retained within a fourth transducer housing 135. In some embodiments, the first and second high frequency bone conductors 130, 133 are smaller in size than the first and second low frequency bone conductors 120, 123 (due to being configured for production of higher-frequency masking tones, as opposed to lower-frequency treatment tones, for example).

Referring particularly to FIGS. 11A-12, the apparatus 10 is shown secured on the head 15 of the user 14, as discussed above with reference to FIGS. 8A-9. As shown, the first and second high frequency bone conductors 130, 133 may be positioned forward of the ears of the user 14 (as compared to the first and second low frequency bone conductors 120, 123, which may be positioned rearward of the ears). For example, the second high frequency bone conductor 133 is shown positioned forward of the right ear 16 of the user 14.

In some embodiments, and shown with reference to FIG. 12, each of the first and second high frequency bone conductors 130, 133 may be configured to be positioned adjacent to and apply at least some pressure to one of the left or right zygoma bones of the user 10. For example, the second high frequency bone conductor 133 is shown to be positioned over the right zygoma bone 20 of the user 14 (e.g., forward of the right ear 16 of the user 14). Of course, one of skill in the art will understand that the left zygoma bone (not shown) is positioned on the opposite side of the head 15 of the user 14, and therefore the first high frequency bone conductor 130 may be positioned over the left zygoma bone of the user 14 (e.g., forward of the left ear of the user 14). The high frequency tone is configured to be transmitted from each of the respective first and second high frequency bone conductors 130, 133 to the associated zygoma bone of the user 14 for masking the tinnitus of the user 14. Thus, in some embodiments, the high frequency tone is at least partially associated with a particular tone of the tinnitus experienced by the user 14.

As shown with reference to FIG. 11B, the second low frequency bone conductor 123 may be located near the bottom of the apparatus 10, as mentioned above with reference to FIG. 8B. The first low frequency bone conductor 120 may be similarly positioned in such alternative embodiments.

Referring to FIGS. 13-20, the apparatus 10 as configured to treat tinnitus using low frequency tones, as well as mask tinnitus using high frequency tones is shown, according to some alternative embodiments of the present disclosure. Referring particularly to FIGS. 13-18, the apparatus 10 may include some or all of the components of the apparatus 10 as discussed above with reference to FIGS. 10-12 (e.g., the apparatus 10 as similarly configured for treating tinnitus using low frequency tones, as well as masking tinnitus using high frequency tones).

As discussed above with reference to FIGS. 10-12, the first and second high frequency bone conductors 130, 133 are smaller in size than the first and second low frequency bone conductors 120, 123. Accordingly, in some embodiments, and as shown, the transducers of the first and second high frequency bone conductors 130, 133 may be small enough to be housed within the material of the first and second sides 102, 104 (respectively) of the apparatus 10, rather than requiring a protruding housing, such as the third and fourth transducer housings 132, 135 depicted with reference to FIG. 10. For example, the first and second high frequency bone conductors 130, 133 may be located at or near the first and second tips 128, 129 (respectively) of the apparatus 10.

Figure 20:
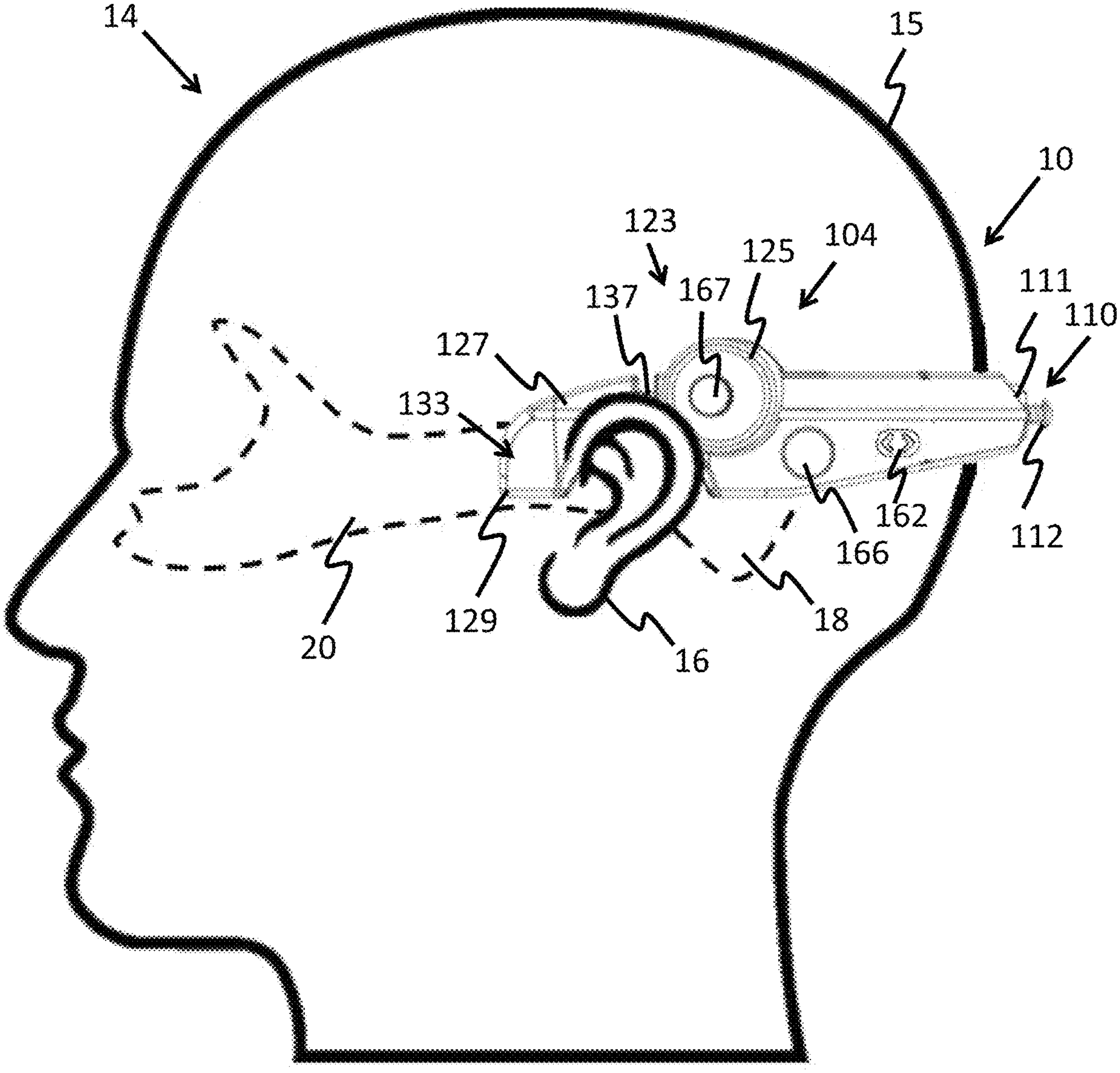
FIG. 20 is a side view of the apparatus of FIG. 13 positioned on a head of a user in accordance with the present disclosure.
Figure 21:
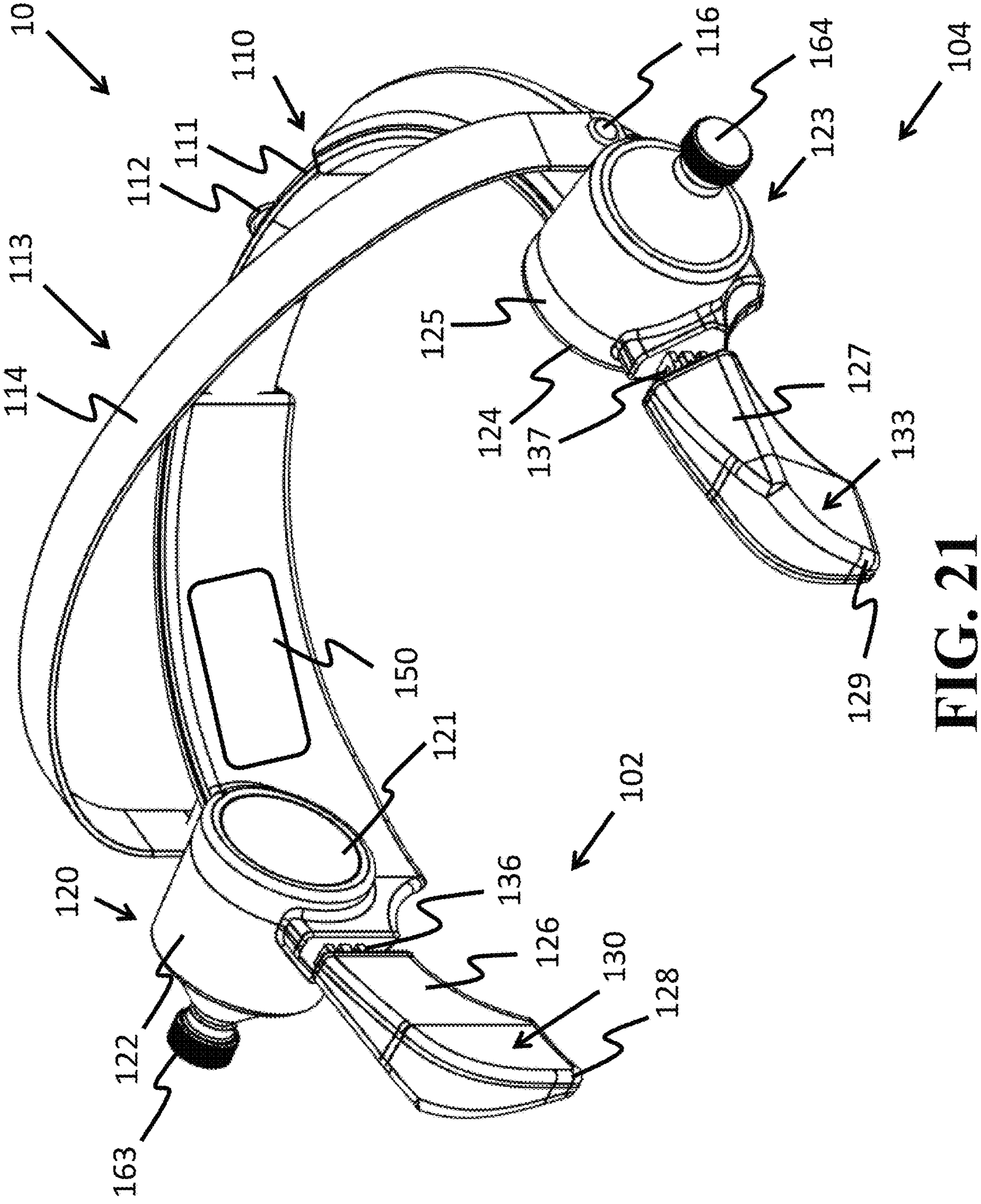
FIG. 21 is a perspective view of the apparatus of FIG. 13 with an over-head strap in accordance with the present disclosure.
Figure 22:
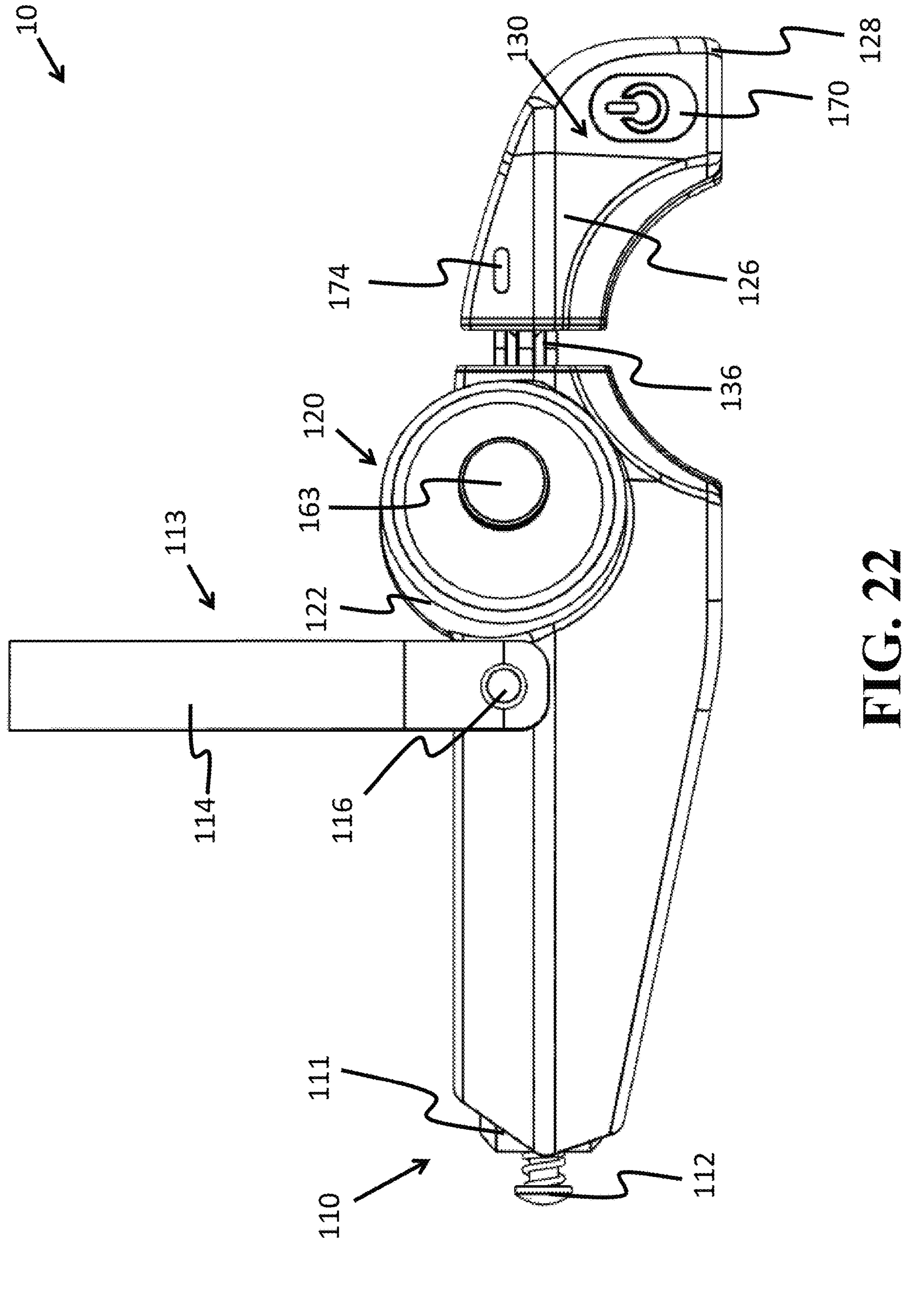
FIG. 22 is a side view of the apparatus of FIG. 13 with an over-head strap in and in accordance with the present disclosure.
Figure 23:
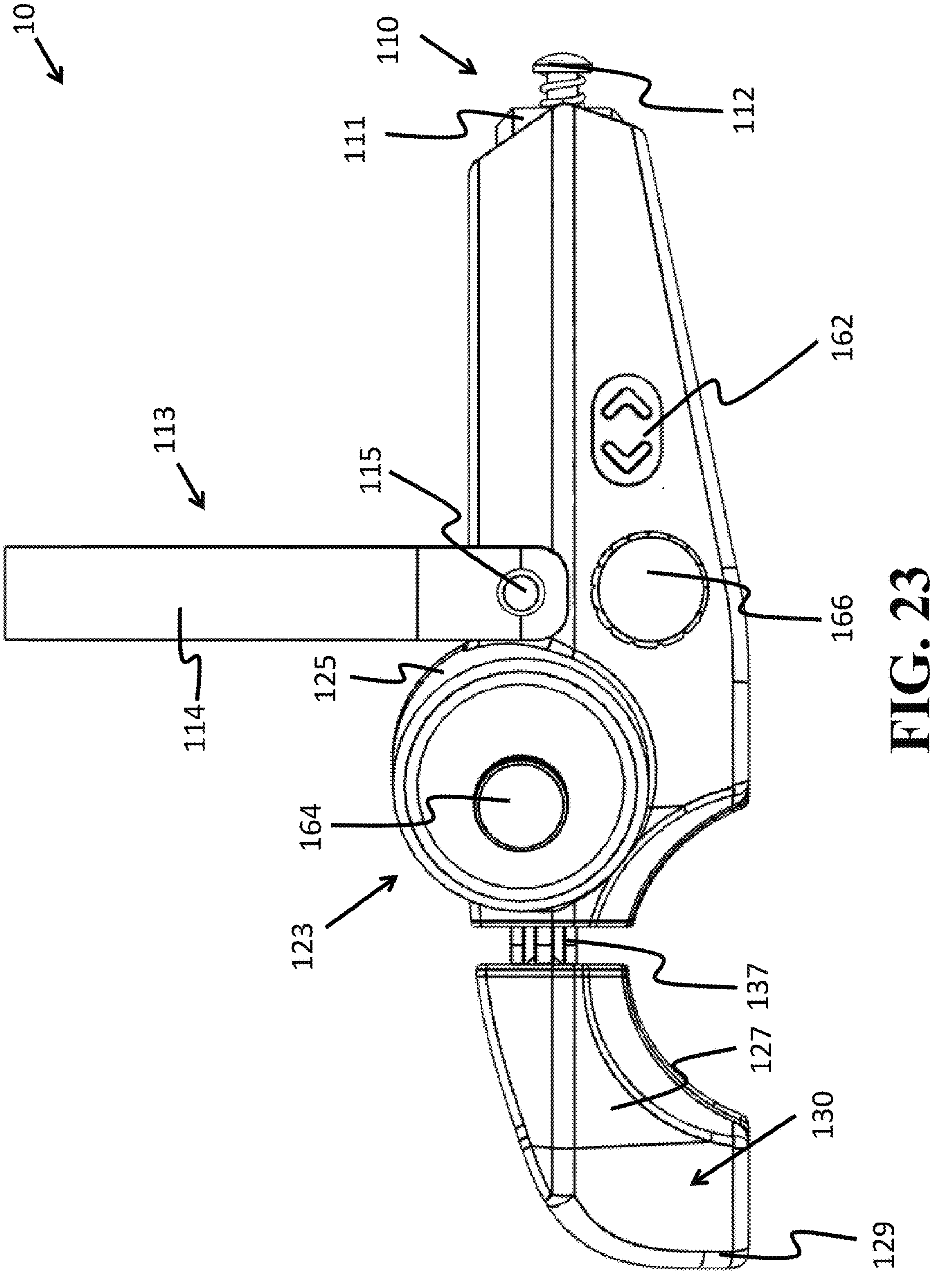
FIG. 23 is a side view of the apparatus of FIG. 13 with an over-head strap in and in accordance with the present disclosure.
Figure 24:
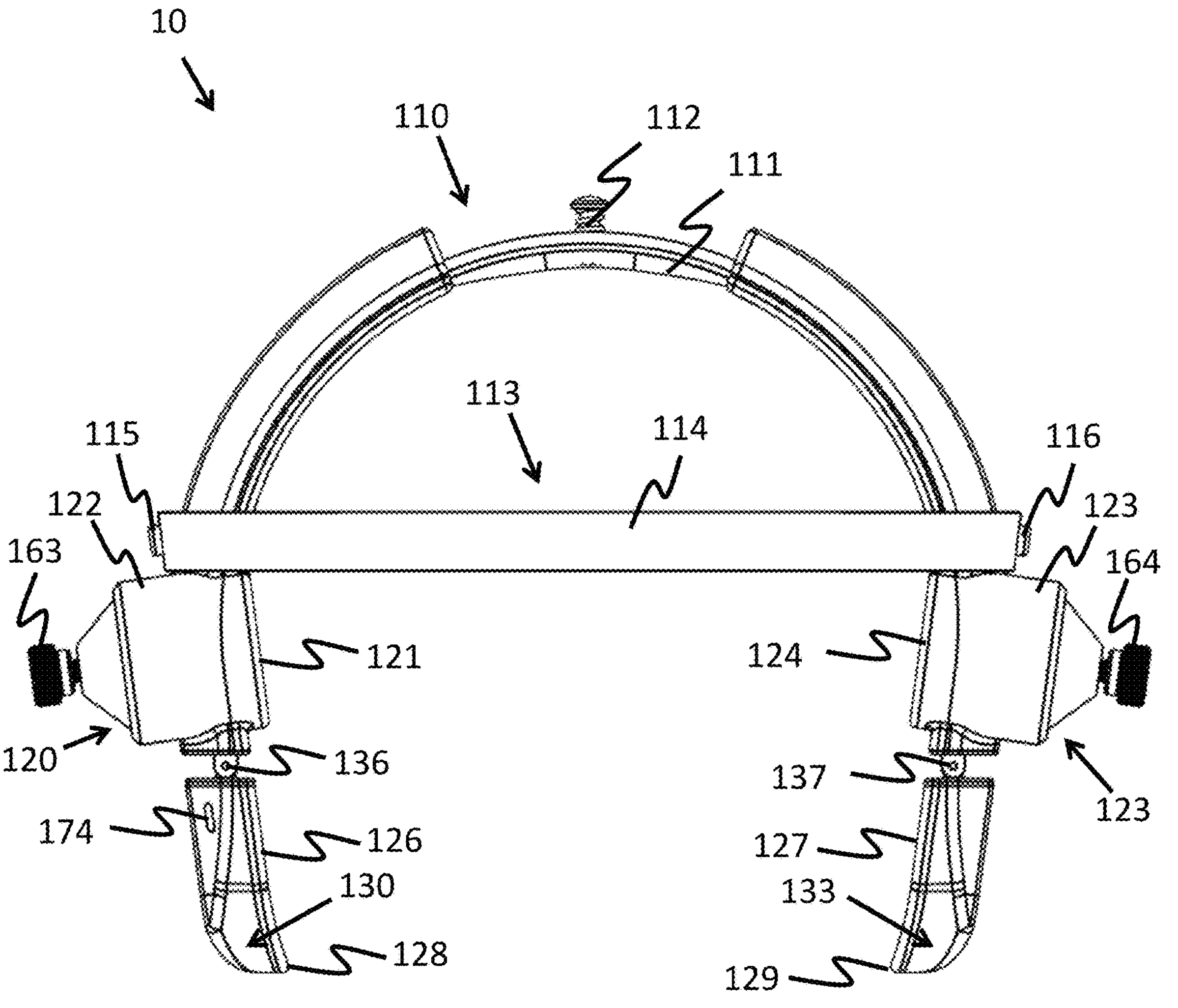
FIG. 24 is a top view of the apparatus of FIG. 13 with an over-head strap in and in accordance with the present disclosure.
Figure 25:
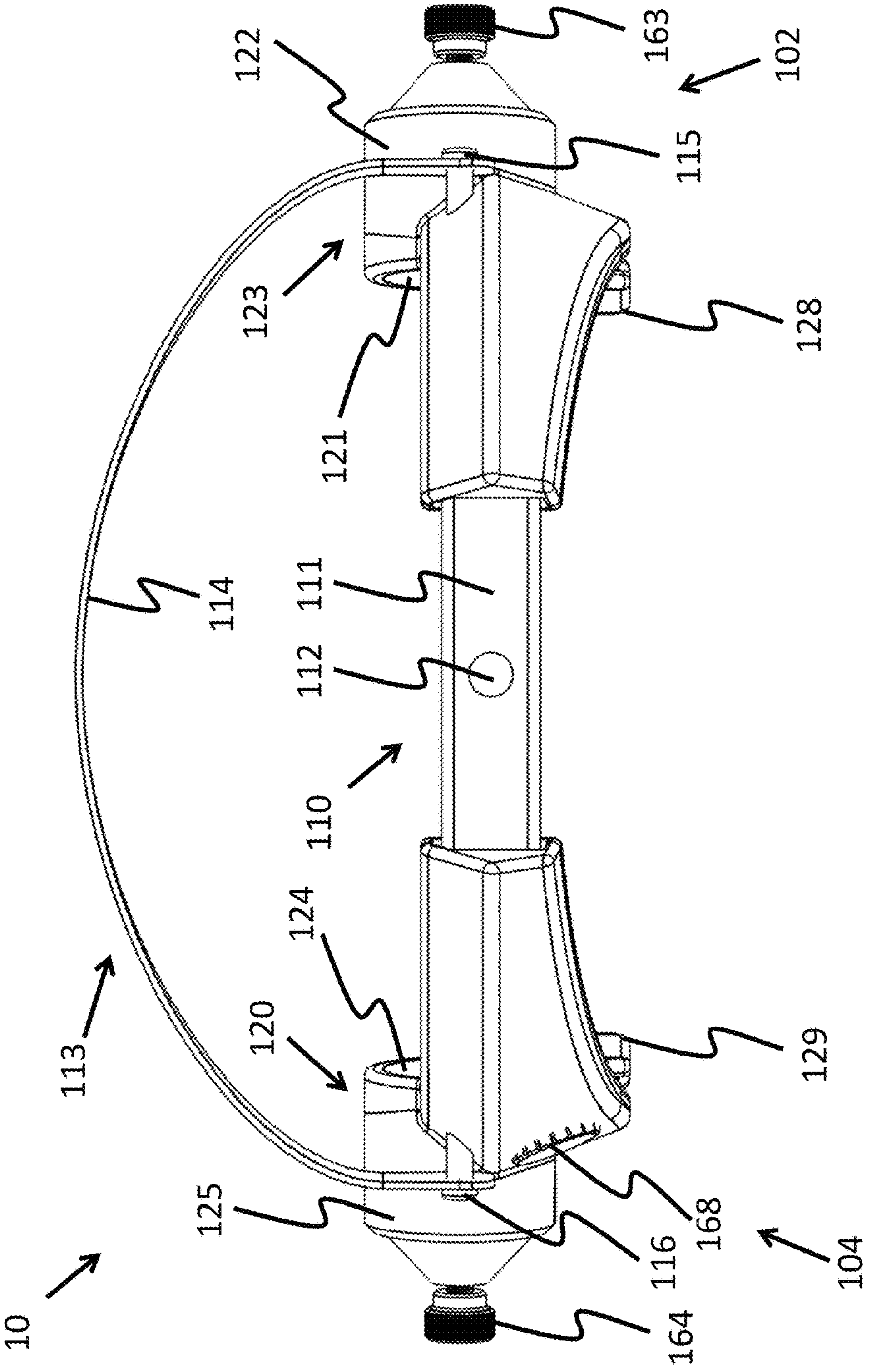
FIG. 25 is a rear view of the apparatus of FIG. 13 with an over-head strap in and in accordance with the present disclosure.
Figure 26:
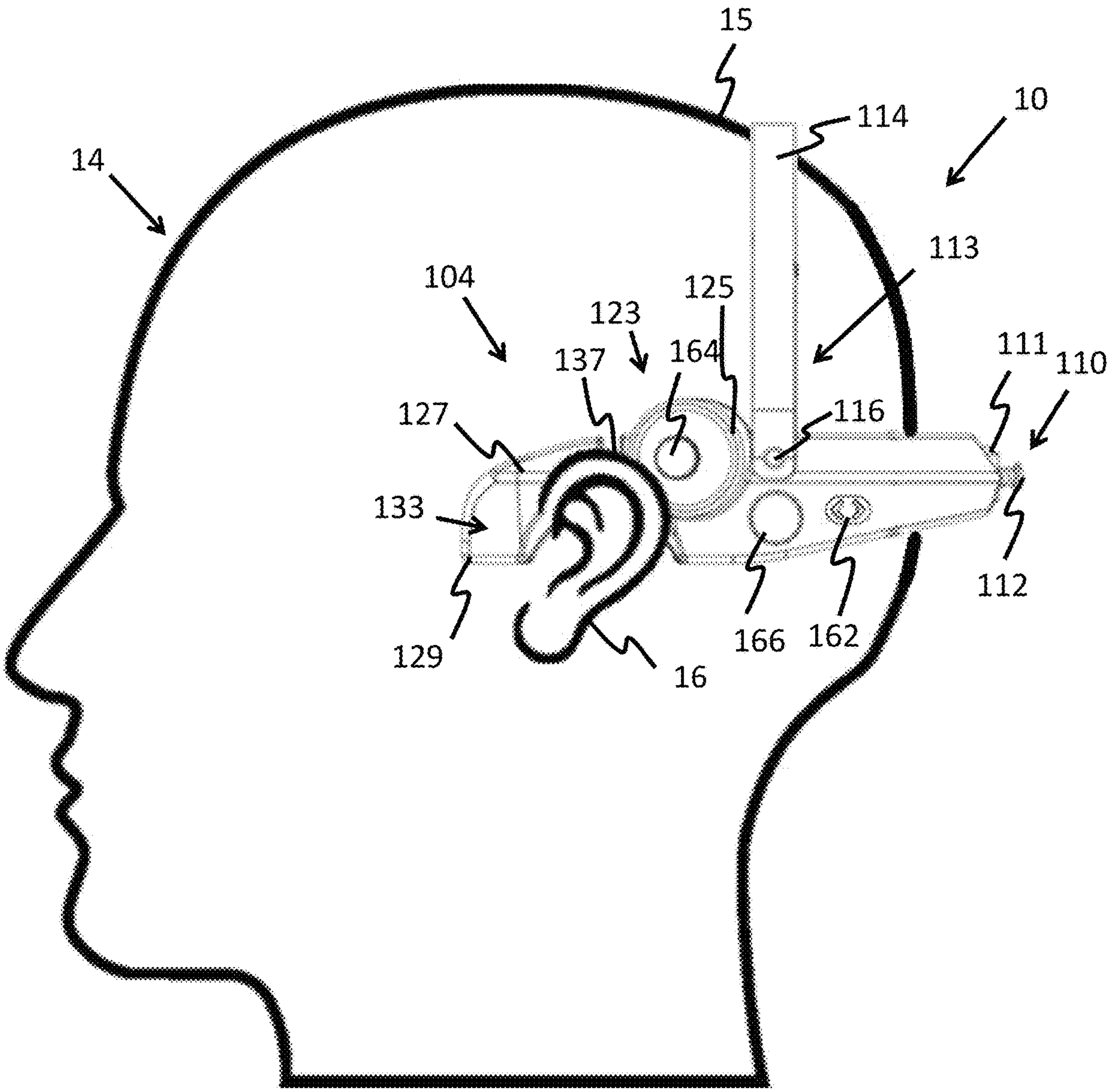
FIG. 26 is a side view of the apparatus of FIG. 13 with an over-head strap in and positioned on a head of a user in accordance with the present disclosure.
Figure 27:
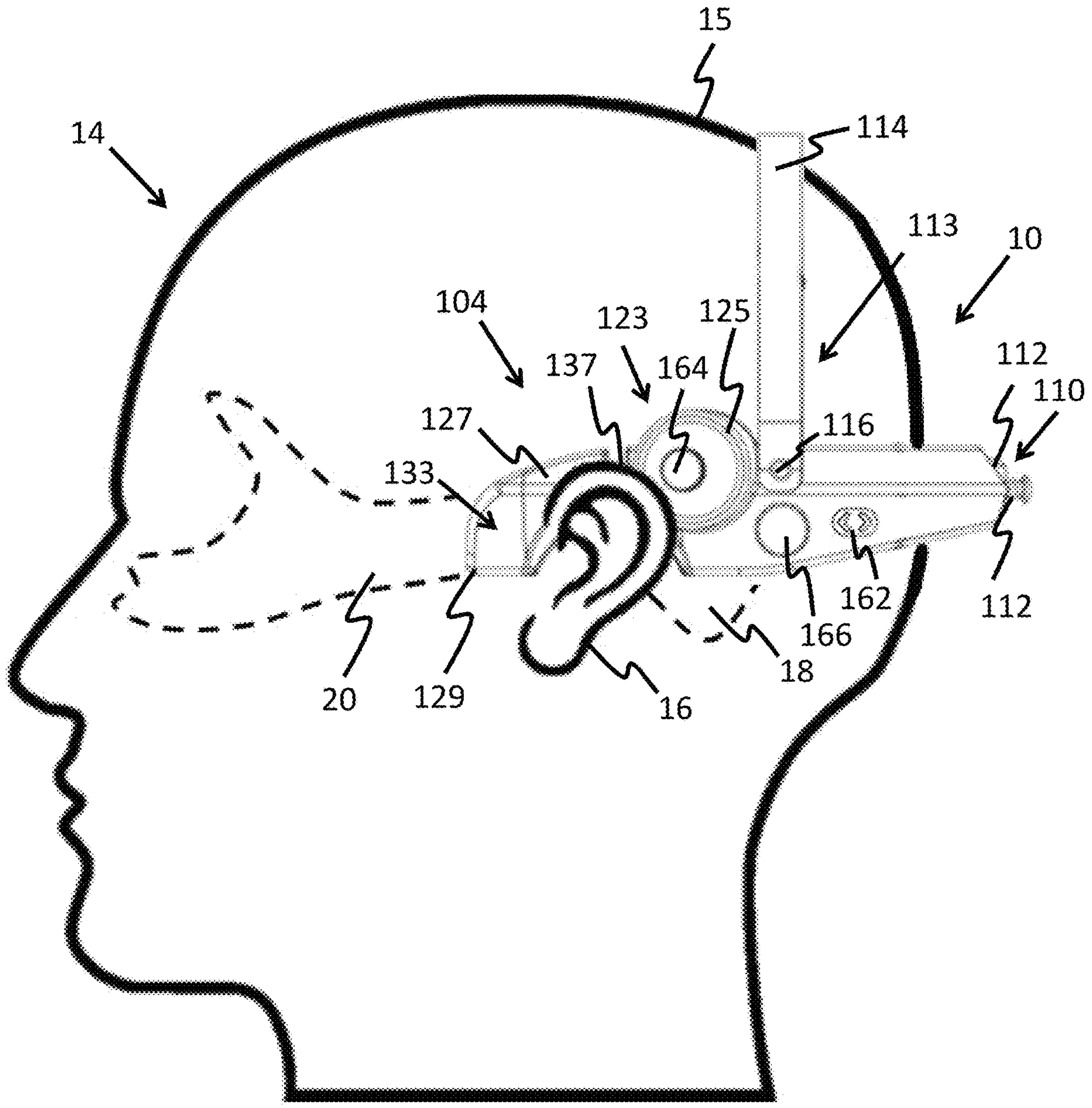
FIG. 27 is a side view of the apparatus of FIG. 13 with an over-head strap in and positioned on a head of a user in accordance with the present disclosure.

In some embodiments, each of the semi-circular strap 110 and the first and second over-ear straps 126, 127 may be adjusted to enable the first and second low frequency bone conductors 120, 123 to apply sufficient pressure to the left and right mastoid bones of the user 14, as well as to enable the first and second high frequency devices 130, 133 to apply sufficient pressure to the left and right zygoma bones of the user 14 (as shown with reference to FIG. 20). As a first example, and as shown with reference to FIG. 16, the first and second over-ear straps 126, 127 may include first and second hinges 136, 137 (respectively). The first hinge 136 may be located between the first low frequency bone conductor 120 and the first high frequency bone conductor 130, and accordingly allow the first high frequency bone conductor 130 (e.g., an orientation thereof) to be pivoted or adjusted with respect to the first low frequency bone conductor 120 and/or the semi-circular strap 110. Similarly, the second hinge 137 be located between the second low frequency bone conductor 123 and the second high frequency bone conductor 133, and accordingly allow the second high frequency bone conductor 133 to the pivoted or adjusted with respect to the second low frequency bone conductor 123 and/or the semi-circular strap 110. As a second example, and as shown with particular reference to FIGS. 17-18, the semi-circular strap 110 may form a rack-and-pinion adjustable section. The rack-and-pinion adjustable section may include a central band 111 that engages each of the first and second sides 102, 104 of the apparatus 10. Accordingly, contours of the central band 111 may be gripped by corresponding contours on the first and second sides 102, 104, until a release button 112 is pressed by the user 14 to disengage the contours of the central band 111, thereby allowing the first and/or second sides 102, 104 to be adjusted relative to the length of the central band 111 and thus increasing or decreasing the positions of the first and second sides 102, 104 relative to one another.

Referring to FIGS. 19-27, the apparatus 10 may further include an over-head retainer 113. Although shown as included in embodiments of the apparatus 10 as depicted with reference to FIGS. 13-20, it should be appreciated that the over-head retainer 113 may be applied to any other embodiment of the apparatus 10 discussed or contemplated herein. The over-head retainer 113 may include a headband 114, a first pivot 115 rotatably coupling the headband 114 to the first side 102 of the apparatus 10, and a second pivot rotatably coupling the headband 114 to the second side 104 of the apparatus 10. Accordingly, the headband 114 may be generally configured to match the contours of the head 15 of the user 14, while also being configured to be pivoted back and forth to provide a secure fit for the user 14, depending on the size of the head 15 of the user 14. In other words, the headband 114 (or an orientation thereof) may be adjusted relative to the semi-circular strap 110.

Figure 28:
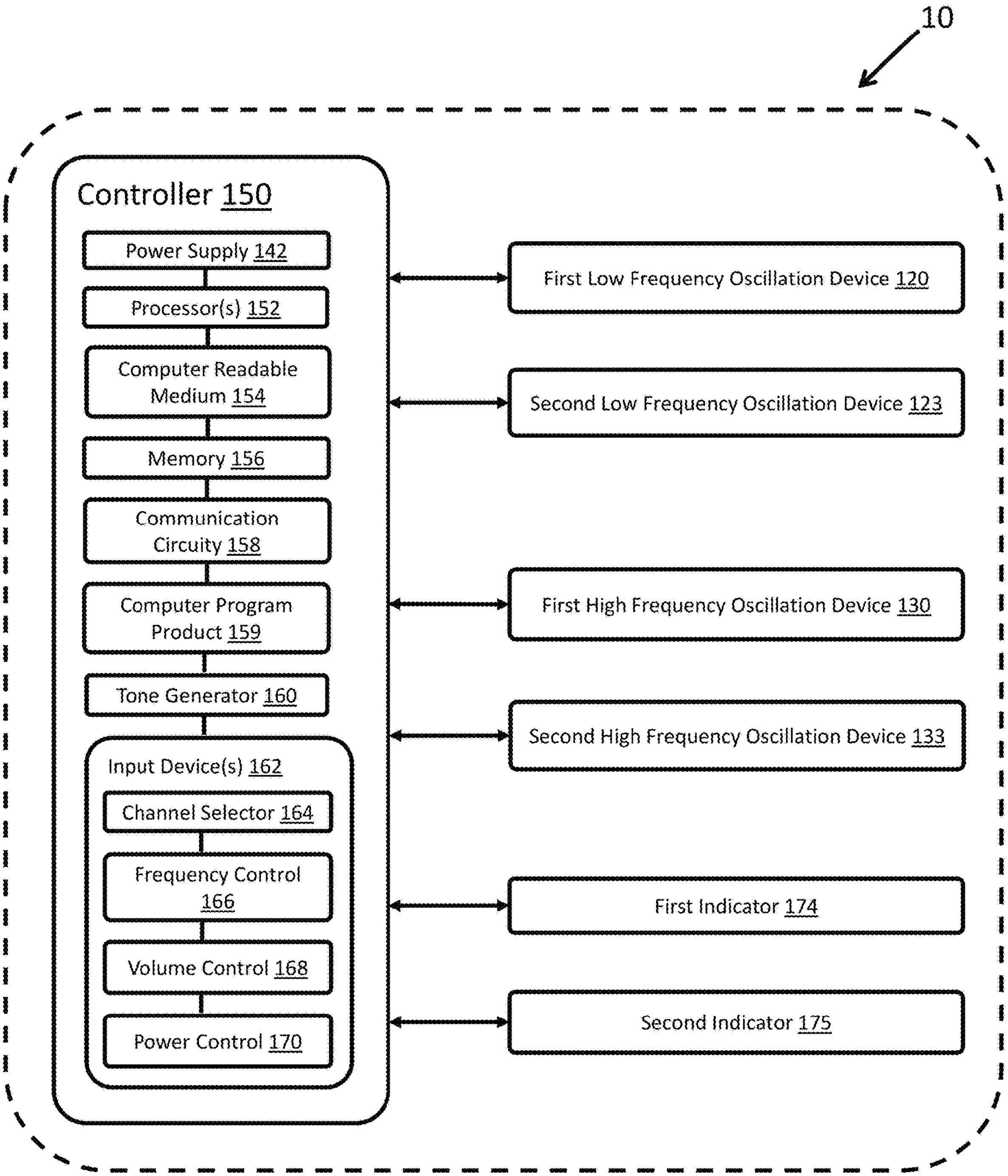
FIG. 28 is a block diagram of the controller of an apparatus for treating tinnitus in accordance with the present disclosure.

Referring to FIG. 28, the controller 150 of the apparatus 10 is depicted in greater detail, according to some embodiments of the present disclosure. Although generally described below as applied to an embodiment of the apparatus 10 that includes each of the first and second low frequency bone conductors 120, 123, as well as the first and second high frequency bone conductors 130, 133, it should be appreciated that the controller 150 and the associated components, systems, and methods discussed below may be applied to embodiments of the apparatus 10 that include only the first and second low frequency bone conductors 120, 123, or solely the first and second high frequency bone conductors 130, 133, depending on the implementation of the present disclosure.

In some embodiments, the controller 150 includes the power supply 142, one or more processors 152, a computer-readable medium 154, a memory 156, communication circuitry 158, a computer program product 159, a tone generator 160, and one or more input devices 161. The processor(s) 152, communication circuitry 158, and memory 156 may collectively be referred to as "logic and control circuitry." The terms "controller" and "control circuitry" as used herein may refer to, be embodied by or otherwise included within a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed and programmed to perform or cause the performance of the functions described herein.

In some embodiments, and as depicted with reference to FIGS. 1, 2, 10, 13, 16, and 21, the controller 150 may be located on the apparatus 10. In other embodiments, and as discussed below with reference to FIGS. 29-32, the controller 150, or some components of the controller 150, are located external to the apparatus 10.

In some embodiments, the power supply 142 is a permanent component within the apparatus 10, provides power to the other components of the apparatus 10, and may be recharged with an external power source. In other words, the power supply 142 may be a permanent battery. In other embodiments, the power supply 142 may be a separate component that is configured to be engaged and/or disengaged from the other components of the apparatus 10, such that the power supply 142 is replaceable. In other words, the power supply 142 may be a replaceable battery. In other embodiments still, the power supply 142 may be provided as an external power source that is engaged (e.g., plugged in) with the other components of the apparatus 10. In other words, the apparatus 10 may be operated by plugging a power chord into a power port located on the apparatus 10.

In some embodiments, the processor(s) 152 include any suitable processing circuitry capable of controlling operations of one or more components of the apparatus 10 (e.g., the first and second low frequency devices 120, 123, the first and second high frequency devices 130, 133, the first and second indicators, etc.). In some embodiments, the processor (s) 152 facilitate communications between various components within the apparatus 10. For example, the processor(s) 152 may receive outputs from the tone generator 160 and convey the outputs to the first and/or second low frequency bone conductors 120, 123, and/or the first and/or second high frequency bone conductors 130, 133. The term "processor" as used herein may refer to at least general-purpose or specific-purpose processing devices and/or logic as may be understood by one of skill in the art, including but not limited to a microprocessor, a microcontroller, a state machine, and the like. A processor can also be implemented as a combination of computing devices, e.g., a combination of a DSP and a microprocessor, a plurality of microprocessors, one or more microprocessors in conjunction with a DSP core, or any other such configuration.

In some embodiments, the computer program product 159 includes a computer-readable storage medium (or media) having computer-readable program instructions thereon for causing a processor to carry out aspects of the present disclosure. For example, as discussed in greater detail below, the computer program product 159 may govern the particular provisions of various high and low frequency tones provided by the first and/or second low frequency bone conductors 120, 123, and/or the first and/or second high frequency bone conductors 130, 133.

In some embodiments, the tone generator 160 includes any suitable processing circuitry capable of converting electrical signals (e.g., control signals provided by the processor(s) 152) into audio signals, which may in turn be provided to the first and/or second low frequency bone conductors 120, 123, and/or the first and/or second high frequency bone conductors 130, 133. Depending on the implementation of the present disclosure, the tone generator 160 may receive one or more electrical signals and convert the one or more electrical signals into one or more audio signals. As a first example, in cases where the various bone conductors are controlled in unison, the tone generator 160 may receive only one electrical signal and respond with only one audio signal (provided to each of the implemented bone conductors(s)). As a second example, however, in cases where the various bone conductors are controlled on an individual basis (in terms of frequency, volume, etc.), the tone generator 160 may receive up to four electrical signals (e.g., one for each bone conductor, depending on the implementation), and respond with up to four audio signals (one for each implemented bone conductor).

In some embodiments, the communication circuitry 158 may include any circuitry capable of connecting the apparatus 10 with one or more external devices, as discussed in greater detail below with reference to FIG. 28. In some embodiments, the memory 156 includes any suitable form of memory such as cache memory, non-transitory memory (e.g., semi-permanent memory, RAM, etc.), or any other memory type, or any combination thereof. In some embodiments, the memory 156 is used in place of and/or in addition to an external memory source or storage unit or device for storing data. The memory 156 may also include one or more storage mediums including, but not limited to, hard drives, solid state drives, flash memory, permanent memory (e.g., ROM), or any other storage type or any combination thereof.

In various embodiments, the input device(s) 161 include a channel selector 162, a first frequency control 163, a second frequency control 164, a third frequency control 164, a fourth frequency control 165, a first volume control 166, a second volume control 167, a third volume control 168, a fourth volume control 169, and/or a power control 170.

In some embodiments, and as shown with reference to FIGS. 5-7, 14, 17, 22 and 24, the apparatus 10 may include first and/or second indicators 174, 175. For example, the first indicator 174 may be located on the first side 102 of the apparatus 10, and the second indicator 175 may be located on the second side 104 of the apparatus 10. The first and second indicators 174, 175 may each be controlled by the controller 150 and include lights that illuminate to signal various operational statuses regarding the function of the apparatus 10. As a first example, the first and/or second indicators 174, 175 may illuminate, flash, or show a particular color to indicate that the apparatus 10 has been activated (e.g., the power control 170 was used to activate the apparatus 10). As a second example, the first and/or second indicators 174, 175 may illuminate, flash, or show a particular color to indicate that the power supply 142 needs to be recharged (e.g., low power of the apparatus 10). As a third example, the first and/or second indicators 174, 175 may illuminate, flash, or show a particular color to indicate some user-originated aspect of control of the apparatus 10 (e.g., updating the frequency or volume of one of the first and/or second low frequency bone conductors 120, 123 and/or the first and/or second high frequency bone conductors 130, 133).

Discussed below are various methods of controlling the apparatus 10 (using the controller 150 and other methods, devices, and systems, depending on the implementation).

Referring again to FIGS. 6-7 and 13-27, the apparatus 10 can be manually controlled by the user 14 via the input device(s) 162 located on the apparatus 10, according to some embodiments of the present disclosure. In such embodiments, the controller 150 as depicted with reference to FIG. 28 may be located on the apparatus 10.

Figure 6:
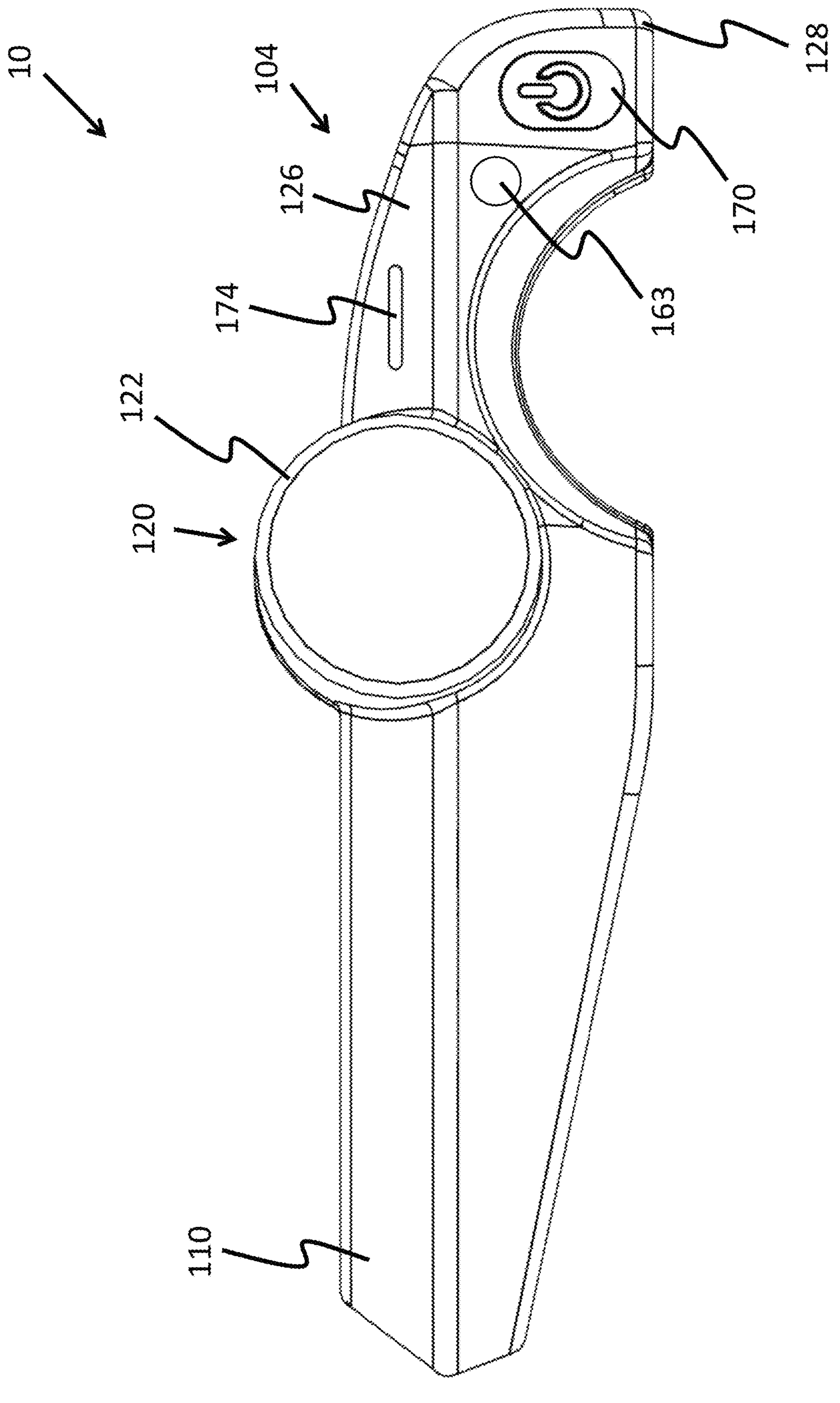
FIG. 6 is a side view of the apparatus of FIG. 1 in accordance with the present disclosure.
Figure 7:
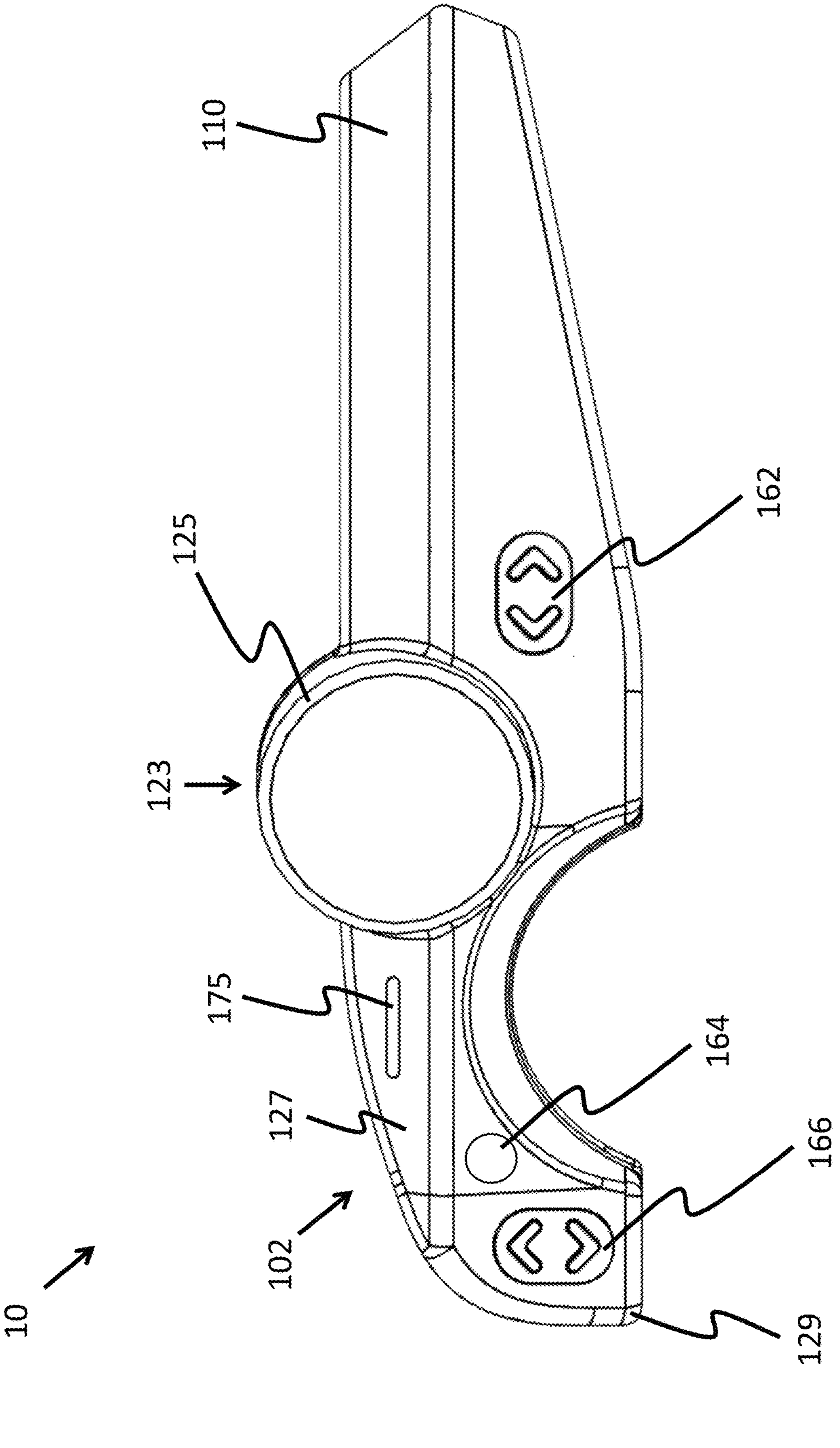
FIG. 7 is a side view of the apparatus of FIG. 1 in accordance with the present disclosure.

Referring particularly to FIGS. 6-7 (depicting the apparatus 10 in an embodiment that includes the first and second low frequency bone conductors 120, 123, while not including the first and second high frequency bone conductors 130, 133), the apparatus 10 may include one or more of the input device(s) 162: the power control (e.g., in the form of an on/off button) 170, the first frequency control 163, the second frequency control 164, the volume control 166, and the channel selector 162. The power control 170 may be used (e.g., pressed by the user 14) in order to activate or de-activate the apparatus 10 (e.g., allow the power supply 142 to provide power to the various components of the apparatus 10 and the controller 150 therein. As shown, the first and second frequency controls 163, 164 may be knobs, and the volume control 166 may be a toggle or pair of buttons. In other embodiments, the first and/or second frequency controls 163, 164, and/or the volume control 166 may be other devices suitable for manual or tactile manipulation by the user 14.

As shown, the power control 170 may be located on the second side 104, while the volume control 166 may be located on the first side 102. Moreover, the first and second frequency controls 163, 164 may be located on or near the first and second over-ear straps 126, 127 (respectively). However, in other embodiments, and as shown with particular reference to FIGS. 13-27, the first and second frequency controls 163, 164 may extend from the first and second transducer housings 121, 122. Further, the power control 170 and/or the volume control 166 may each be located on a different one of the first and second sides 102, 104. It should be appreciated that the various control devices discussed herein may be positioned at any suitable point on the apparatus 10, and the particular locations of the control devices as depicted herein are merely shown as exemplary, non-limiting embodiments.

In some embodiments, the first and second frequency controls 163, 164 allow the user 14 to manually increase or decrease the frequency (e.g., hertz) of the tones provided by the first and second low frequency bone conductors 120, 123 (respectively). In this sense, the frequencies of the tones provided by the first and second low frequency bone conductors 120, 123 may be individually controlled. For example, the first low frequency bone conductor 120 may be operated to provide a tone at fifty hertz, while the second low frequency bone conductor 123 may be simultaneously operated to provide a tone at sixty hertz. In other embodiments, only one of the first and second frequency controls 163, 164 are provided on the apparatus 10. In some cases of such embodiments, the first and second low frequency bone conductors 120, 123 are be operated at, and simultaneously adjusted to, the same frequency. In other cases of such embodiments, the channel selector 162 is used to toggle which of the bone conductors between the first and second low frequency bone conductors 120, 123 are operated by the single frequency control. For example, the single frequency control may be operated to adjust the frequency of the first low frequency bone conductor 120, the channel selector 162 may be pressed to toggle the control over to the second low frequency bone conductor 123, and then the single frequency control may be operated to adjust the frequency of the second low frequency bone conductor 123.

In some embodiments, the volume control 166 may be used to increase or decrease the volume (in decibels for example) of the first and second low frequency bone conductors 120, 123. In some embodiments, the volume of the first and second low frequency bone conductors 120, 123 may be set to approximately forty decibels (or adjusted thereabout) in order for the tones produced by the first and second low frequency bone conductors 120, 123 to be perceptible to the user. In some embodiments, and as shown, there may be only one volume control 166 on the apparatus 10. In such cases, as discussed above with reference to embodiments of the apparatus 10 that include a single frequency control, the channel selector 162 may be used to toggle the control applied by the volume control 166 between the first and second low frequency bone conductors 120, 123.

As shown with particular reference to FIGS. 13-27 (depicting the apparatus 10 in an embodiment that includes the first and second low frequency bone conductors 120, 123, as well as the first and second high frequency bone conductors 130, 133), the apparatus 10 may similarly include one or more of the input device(s) 162: the power control (e.g., in the form of an on/off button) 170, the first frequency control 163, the second frequency control 164, the volume control 166, and the channel selector 162. One or more of the aforementioned input device(s) 162 may also be included on the apparatus 10 as depicted with reference to FIG. 10.

In some embodiments, the first and second frequency controls 163, 164 allow the user 14 to manually increase or decrease the frequency of the tones provided by the first and second low frequency bone conductors 120, 123 and the first and second high frequency bone conductors 130, 133 in a fashion similar to that which is described above. In some arrangements, and as shown, there are only two frequency controls (the first and second frequency controls 163, 164), while the apparatus 10 includes four bone conductors (the first and second low frequency bone conductors 120, 123 and the first and second high frequency bone conductors 130, 133). In some cases of such arrangements, the frequencies of each of the first low frequency bone conductor 120 and the first high frequency bone conductor 130 are simultaneously adjusted by the first frequency control 163, while the frequencies of each of the second low frequency bone conductor 123 and the second high frequency bone conductor 133 are simultaneously adjusted by the second frequency control device 164. In other cases of such arrangements, the channel selector 162 may be used to simultaneously toggle the control applied by the first frequency control 163 between the first low frequency bone conductor 120 and the first high frequency bone conductor 130, as the control applied by the second frequency control 164 between the second low frequency bone conductor 123 and the second high frequency bone conductor 133. In other arrangements, there are four frequency controls, each applicable to one of the first and second low frequency bone conductors 120, 123 and the first and second high frequency bone conductors 130, 133.

In some embodiments, the volume control 166 may be used to increase or decrease the volume of the first and second low frequency bone conductors 120, 123 and the first and second high frequency bone conductors 130, 133 in a fashion similar to that which is described above. In some arrangements, and as shown, there is only the one volume control 166, while the apparatus 10 includes four bone conductors (the first and second low frequency bone conductors 120, 123 and the first and second high frequency bone conductors 130, 133). In some cases of such arrangements, the volumes of each of the first and second low frequency bone conductors 120, 123 and the first and second high frequency bone conductor 130, 133 are simultaneously adjusted by the volume control 166. In other cases of such arrangements, the channel selector 162 may be used to toggle the control applied by the volume control 166 between each of the first and second low frequency bone conductors 120, 123 and the and second high frequency bone conductors 130, 133. In other arrangements, there are four volume controls, each applicable to one of the first and second low frequency bone conductors 120, 123 and the first and second high frequency bone conductors The various controls for manual operation of the apparatus 10 as discussed above in relation to FIGS. 13-27 may similarly be implemented in embodiments of the apparatus 10 as depicted with reference to FIGS. 10-12 (which similarly includes the first and second low frequency bone conductors 120, 123, as well as the first and second high frequency bone conductors 130, 133).

Figure 29:
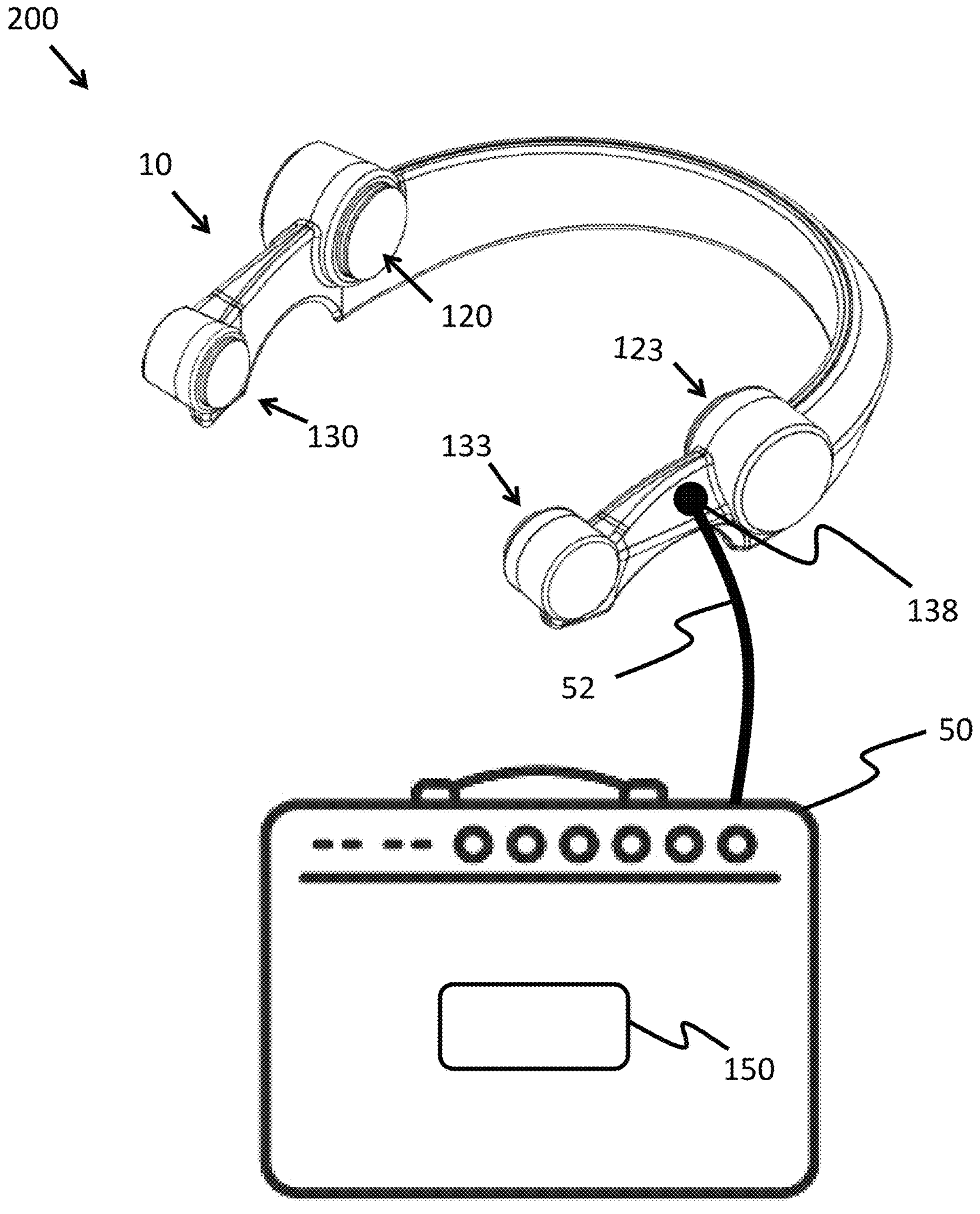
FIG. 29 is an apparatus for treating tinnitus in communication with an external control device in accordance with the present disclosure.

Referring to FIG. 29, the apparatus 10 can be externally controlled by the user 14 in a system 200, according to some embodiments of the present disclosure. The system 200 may include the apparatus 10 as discussed herein, and an external device 50 (e.g., a control device apart from the apparatus 10). The external device 50 may communicate with the apparatus 10 via a cord 52 (e.g., a wired connection) that extends from the external device 50 to a port 138 on the apparatus 10. In some embodiments, some or all of the components of the controller 150 as depicted with reference to FIG. 28 may be located on the apparatus 10. As a first example, and as shown, the entirety of the controller 150 may be located on the external device 50. As a second example, the tone generator 160 may be located on the apparatus 10, while the remaining components of the controller 150 are located on the external device 50. As a third example, some or all of the input device(s) 162 may be located on the external device 50, while the remaining components of the controller 150 are located on the apparatus 10. Similar to the discussion of the various input device(s) 162 above, the external control device 150 may include various frequency control(s), volume control(s), the power control 170, and the channel selector 162 (in cases where there are not corresponding frequency or volume controls for each of the implemented bone conductors).

Figure 30:
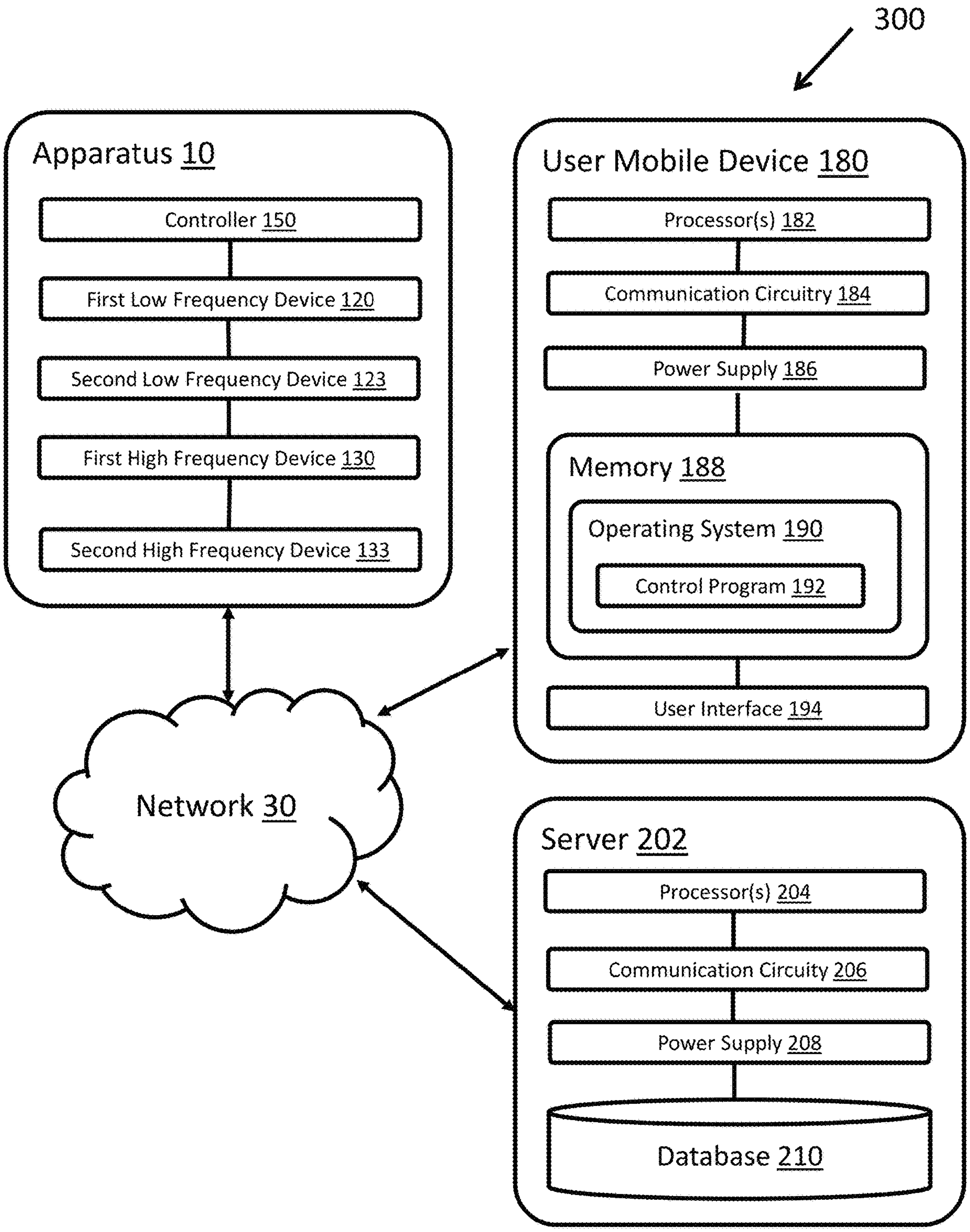
FIG. 30 is a block diagram of a system for treating tinnitus including a headset apparatus, a mobile device, and a server in accordance with the present disclosure.

Referring to FIGS. 30-35, the apparatus 10 can be remotely controlled by the user 14 in a system 300, according to some embodiments of the present disclosure. Referring particularly to FIG. 30, the system 300 may include the apparatus 10 as discussed herein and a user mobile device 180. In some embodiments, the system 300 further includes a server 202. As described in greater detail below, the apparatus 10 may communicate with the user mobile device 180 and/or the server 202 over a network 30. As examples, the network 30 may be a local area network ("LAN"), a wide area network ("WAN"), a point-to-point network, and so on.

In some embodiments, the apparatus 10 includes the components described above with respect to FIG. 28 (e.g., the first and second low frequency bone conductors 120, 123, the first and second high frequency bone conductors 130, 133, the controller 150, etc.); the user mobile device 180 includes one or more processors(s) 182, communication circuitry 184, a power supply 186 (which may operate in a similar fashion to the power supply 142), a memory 188, and a user interface 194; and the server 202 includes one or more processor(s) 204, communication circuitry 206, a power supply 208 (which may operate in a similar fashion to the power supplies 142, 208), and a database 210.

Depending on the implementation of the present disclosure, the user mobile device 180 may be a desktop computer, a laptop computer, a tablet computer, a wireless device such as a mobile phone or a smart phone, a smartwatch, a gaming console, an application server, a database server, or some other type of computing device. The user mobile device 180 may include a physical computing device or may include a virtual machine executing on another computing device. In conjunction with the server 202, the user mobile device 180 may form a cloud computing system, a distributed computing system, or another type of multi-device system.

In some embodiments, the communications circuitries 158, 184, and 206 of the apparatus 10, the user mobile device 180, and the server 202 (respectively) each include any circuitry capable of connecting the apparatus 10, the user mobile device 180, and the server 202 with one or more external devices, including each other. Accordingly, the communication circuitries 158, 184, and 206 may include any circuitry capable of connecting the apparatus 10, the user mobile device 180, and the server 202 (respectively) to the network 30 and with each other over the network 30. The communication circuitries 158, 184, and 206 may support any suitable communications protocol including, but not limited to, Wi-Fi (e.g., 802.11 protocol), Bluetooth®, radio frequency systems (e.g., 900 MHz, 1.4 GHz, and 5.6 GHz communications systems), infrared, GSM, GSM plus EDGE, CDMA, quadband, VOIP, or any other communications protocol, or any combination thereof. Thus, one or more of the communications circuitries 158, 184, and 206 may be configured for a wireless connection, as shown. In other embodiments, one or more of the communications circuitries 158, 184, and 206 are configured for a wired connection, as depicted above with reference to the apparatus 10 as shown in FIG. 29.

In some embodiments, the memories 156 and 188 of the apparatus 10 and the user mobile device 180 (respectively) may each store various data structures and/or modules in order to perform the systems and methods described herein. Similarly, the database 210 of the server 202 may include one or more data structures for performing the systems and methods described herein. For example, in order for the apparatus 10 to function in accordance with the systems and methods described herein, the apparatus 10 may receive stored data from the user mobile device 180 and/or the server 202. Pursuant to such systems and methods, the apparatus 10 may store, at least temporarily, such received data. In some embodiments, the memory 188 of the user mobile device 180 stores data regarding the user 14 and/or an operating system 190, which includes a control program 192. As described in greater detail below, the control program 192 may (via the user interface 194) display one or more graphical user interfaces ("GUI(s)") and perform operations relating the systems and methods described herein.

Figure 31:
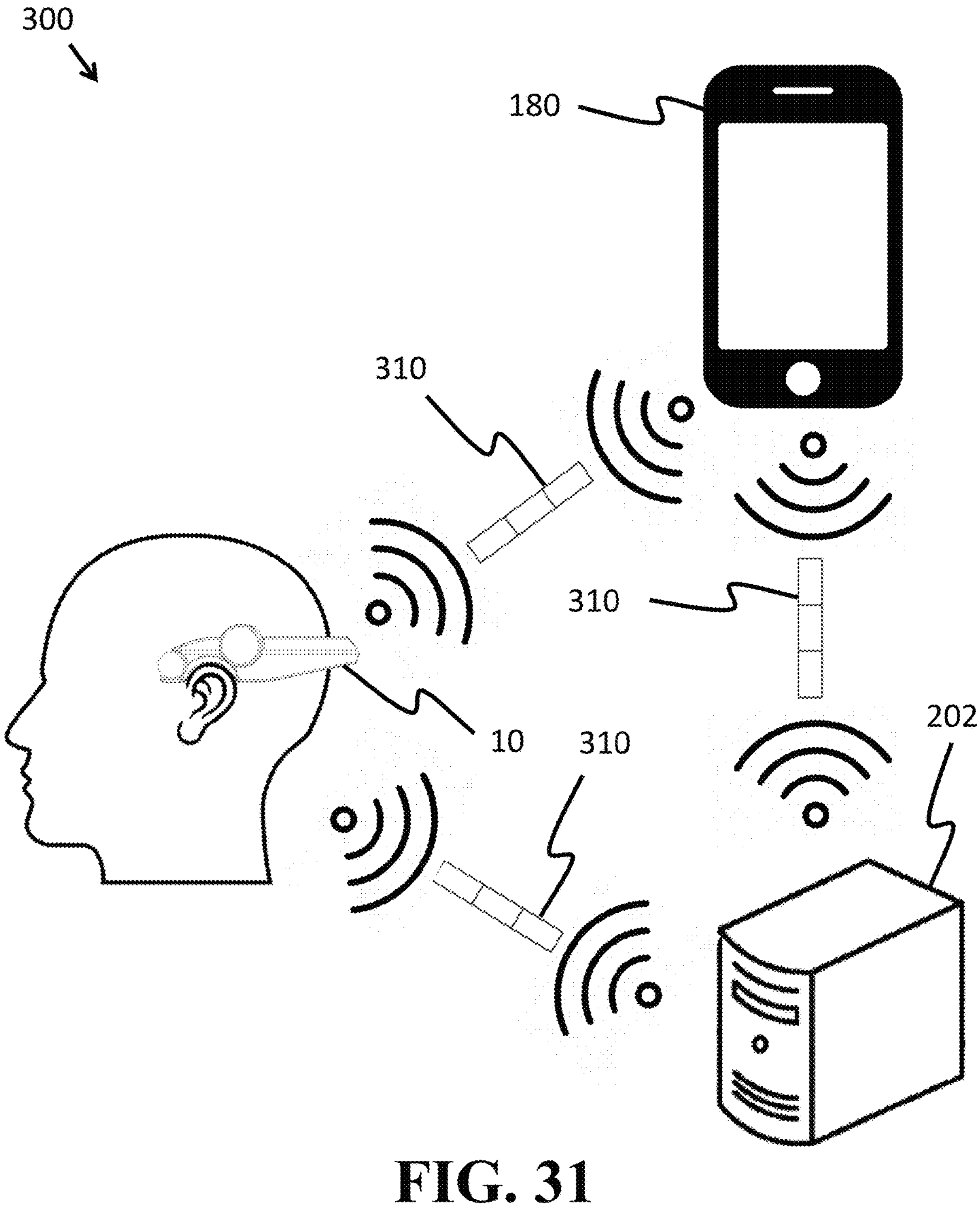
FIG. 31 is a schematic diagram of the system of FIG. 30 in accordance with the present disclosure.

Referring particularly to FIGS. 31-32, the system 300 is shown in greater detail, according to some embodiments of the present disclosure. As discussed above, the apparatus 10 may control the operation of the first and second low frequency bone conductors 120, 123 and the first and second high frequency bone conductors 130, 133 by receiving data from the user mobile device 180 and/or the server 202. Advantageously, by leveraging the user mobile device 180 and/or the server 202 as discussed below, the apparatus 10 may be operated in a customize-able and/or individualized fashion in order to provide enhanced treatment and/or masking of the tinnitus of the user 14.

As shown, the apparatus 10 may receive data from the user mobile device 180 and/or the server 202 in the form of one or more data packets 310. Each data packet 310 may include a list of data that is interpretable by the apparatus 10 for controlling the various components therein. For example, and as shown with reference to FIG. 32, a single data packet 310 may include, for each of the various bone conductors, an on/off value, a volume value, and a frequency value.

In some embodiments, a single data packet 310 may indicate, for each of the bone conductors, a series of control values to be applied by the apparatus 10 for an indefinite period of time (e.g., until another data packet 310 is received by the apparatus 10 indicating a change in the control values). In other embodiments, a single data packet 310 may indicate, for each of the bone conductors, a series of control values to be applied for a specific amount of time (0.01 seconds, 0.1 seconds, 0.5 seconds, 1 second, etc.) before a new data packet 310 is expected to be received and/or applied by the apparatus 10. In this sense, various control values may be "streamed" to the apparatus 10 by the user mobile device 180 and/or the server 202. In other embodiments still, a series of data packets 310 may be received by the apparatus 10 from the user mobile device 180 and/or the server 202, each with a series of control values and configured to be evaluated together, in order, to compile a programmed session of the apparatus 10 as described above. In this sense, the apparatus 10 may receive a number of data packets 310 from the user mobile device 180 and/or the server 202 which, when applied by the apparatus 10 in order, form a programmed session of the apparatus 10.

As suggested above, by receiving and effectuating multiple data packets 310, the apparatus 10 may perform various programmed sessions for tinnitus treatment. As a first example, variables of operation of the apparatus 10, such as frequency of the various bone conductors, may go through "sweeps" (e.g., fluctuations) across a range of values. Such sweeps may be carried out sinusoidally, step-wise, and in accordance with other various algorithms in order to optimize treatment and/or masking of tinnitus. Moreover, the one or more of the bone conductors may be operated to the exclusion of one or more of the other bone conductors. Accordingly, it should be appreciated that numerous patterns of applying the low and high frequency tones as discussed herein may be provided by the apparatus 10 in order to treat and/or mask tinnitus.

Figure 33:
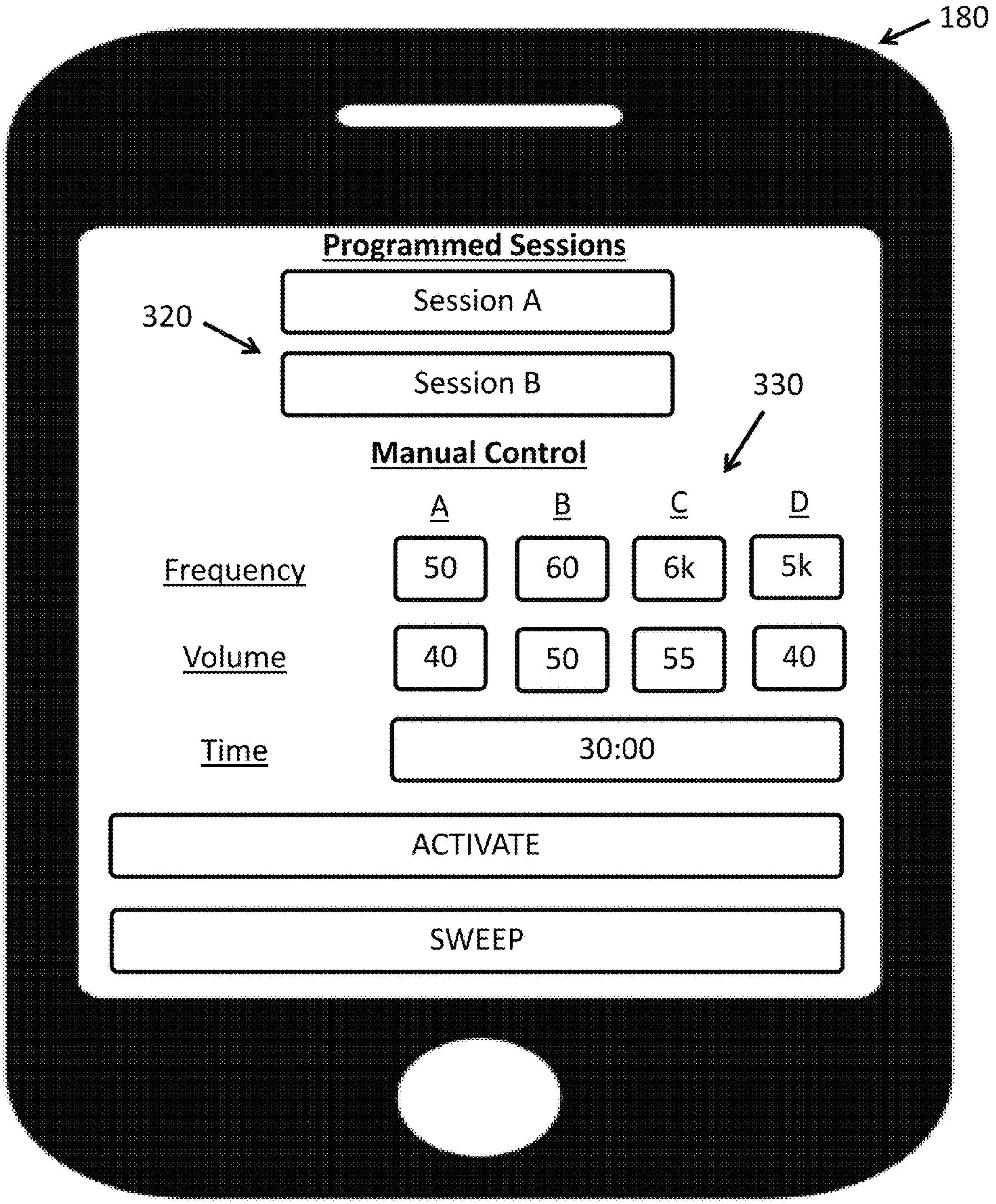
FIG. 33 is a schematic diagram of a control program of the mobile device of the system of FIG. 30 in accordance with the present disclosure.
Figure 34:
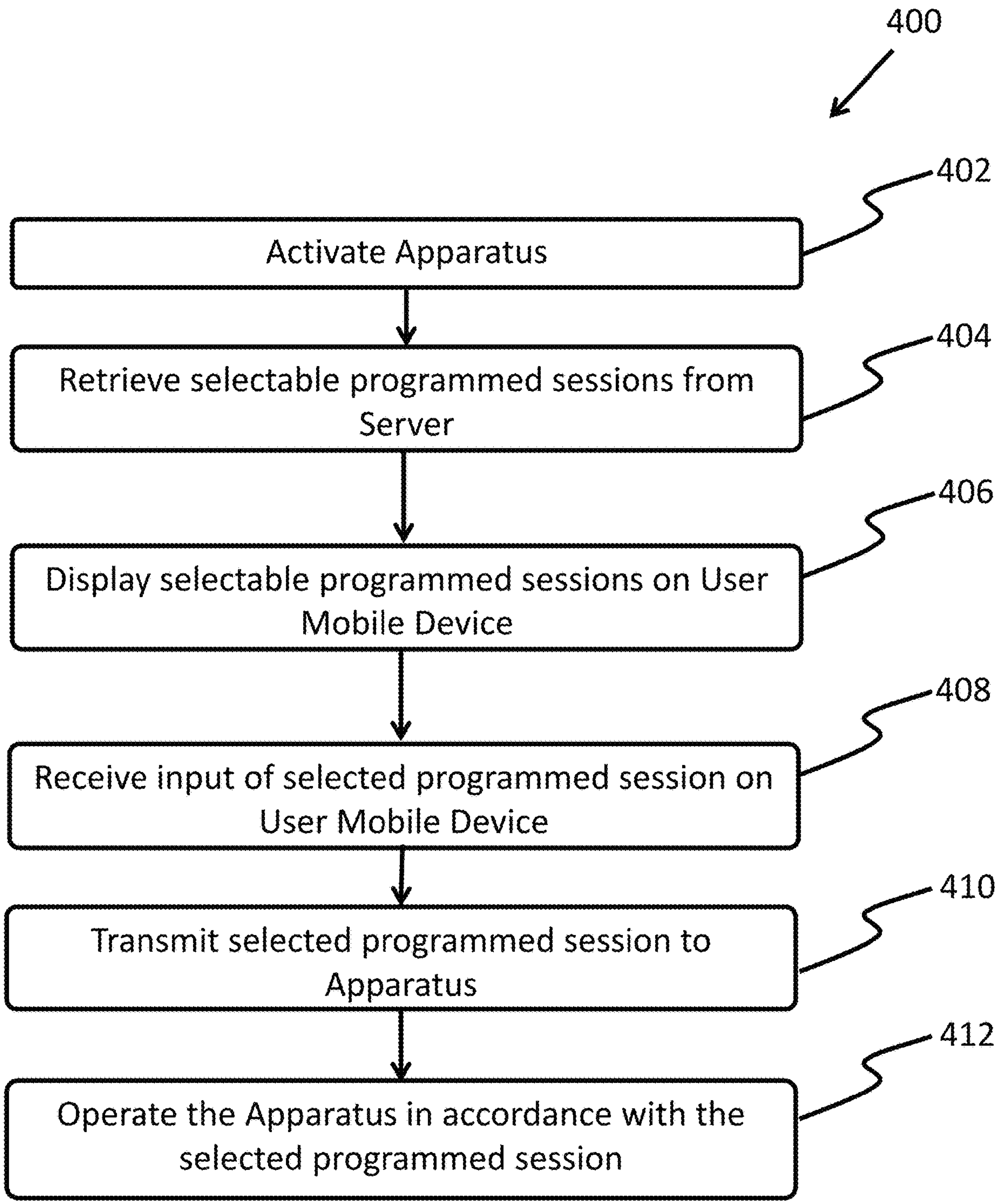
FIG. 34 is a flow diagram of a method of treating tinnitus in accordance with the present disclosure.

Referring particularly to FIG. 33, the control program 192 on the user mobile device 180 may, via one or more GUIs displayed on the user interface 194, allow the user 14 to select one or more programmed sessions (e.g., programmed sessions, control patterns, etc.) 320 or make one or more manual control selections 330 in order to operate the apparatus 10. In some embodiments, upon opening activation of the control program 192, the user mobile device 180 may communicate with the server 202 to retrieve the programmed sessions 320 for display. In other embodiments, the user mobile device 180 stores such programmed sessions 320 in the memory 188 of the user mobile device 180 and may automatically display the programmed sessions 320.

In some embodiments, the control program 192 may allow a user to manually input the various control metrics (e.g., frequency and/or volume of the tones produced by the first and/or second low frequency bone conductors 120, 123 and/or the first and/or second high frequency bone conductors 130, 133) via the manual control selections 330 for operation of the apparatus 10. For example, via the control program 192, the first low frequency bone conductor 120 may be identified as "A," the second low frequency bone conductor 123 may be identified as "B," the first high frequency bone conductor 130 may be identified as "C," the second high frequency bone conductor may be identified as "D," the frequency and volume for each of the various bone conductors may be set, a pre-determined amount of time for the duration of operation of the apparatus 10 under such control variables may be set, and such control may be activated. In this sense, the control program 192 may be operated similar to the use the first frequency control 166, the second frequency control 167, and/or the volume control 166 located on the apparatus 10 as depicted with reference to FIGS. 6, 7, 14, and 15. Thus, low frequency tones may be administered by the first and second low frequency bone conductors 120, 123 among various variables for a pre-determined time period. Similarly, high frequency tones may be administered by the first and second high frequency bone conductors 130, 133 among various variables for a pre-determined time period.

As suggested above, the manual control selections 330 may allow the user 14 to select a "sweep" of the various control metrics. For example, the user mobile device 180 may transmit various data packets 310 to the apparatus 10 to gradually increase or decrease the operating frequencies and/or volumes of the first and/or second low frequency bone conductors 120, 123 and/or the first and/or second high frequency bone conductors 130, 133. The user 14 may perceive the various sweeping changes to the control variables until the user 14 perceives an operational variable that the user 14 prefers (e.g., for treatment of tinnitus, for masking tinnitus, etc.). The user 14 may then stop the sweep (e.g., by re-selecting the sweep option on the manual control selections 330) and save one or more of the various control metrics to be later selected as one of the pre-selected treatments 320. Furthermore, the user 14 may select a particular sweep across a range of particular variables for a particular amount of pre-determined time.

In some embodiments, one or more selections of control variables may be saved to later be selected as a programmed session 320 (e.g., "Session A," "Session B," and so on). Thus, the control program 192 may allow a user to select a particular pattern of control metrics for operation of the apparatus 10. For example, and as suggested herein, there are a number of variables relating to the operation of the apparatus 10. As a first example, the frequency and volume of the first and second low frequency bone conductors 120, 123 and/or the first and second high frequency oscillation device 130, 133 may not only be variable selected, but vary over a pre-determined amount of time. As a first example, the pre-determined amount of time for administration of the low and high frequency tones via the apparatus 10 may be one minute. As a second example, the pre-determined amount of time may be fifteen minutes. In this sense, one of the bone conductors may start at a particular frequency, increase in frequency, decrease in frequency, and so on, over a particular span of time. Additionally, the operation of the various bone conductors in a binary sense (producing tones versus not producing tones whatsoever) may be varied over a span of time. In this sense, the first and second low frequency bone conductors 120, 123 may be operated while the first and second high frequency bone conductors 130, 133 are not (and vice-versa); the first low and high frequency devices 120, 130 (e.g., the bone conductors on the first side 102 of the apparatus 10) may be operated while the second low and high frequency devices 123, 133 (e.g., the bone conductors on the second side 104 of the apparatus 10) are not; the second high frequency bone conductor 133 may be operated while the other bone conductors are not; and so on. The above variable aspects of operating the apparatus 10 may all be variably controlled over time in a specific pattern by the control program 192.

Thus, a set of control variables for a particular duration of time may be selected and saved as a programmed session 320, or multiple sets of control variables for multiple durations of time (e.g., one minute, fifteen minutes, etc.) may be selected and saved as a single programmed session 320. Further, the control program 192 may allow other customization options such as editing one of the pre-existing programmed sessions 320. In some embodiments, one or more of the programmed sessions 320 are supplied (e.g., pre-configured) by the control program 192. In some cases, some or all of the programmed sessions 320 may be retrieved form the database 210 of the server 202. As discussed in greater detail below, some of such pre-configured programmed sessions 320 may be "trial" sessions that can be used to evaluate the tinnitus of the user 14 or the treatment/masking preferences of the user 14.

As discussed above with reference to FIG. 33, the user mobile device 180 may facilitate the selection and use of one of the programmed sessions 320. Accordingly, and referring particularly to FIG. 34 with additional reference to FIG. 33, the control program 192 of the user mobile device 180 may facilitate a method 400 of using one or more of the programmed sessions 320.

In a first step 402 of the method 400, the apparatus 10 may be activated by the user 14. Before or after activation of the apparatus 10, the user 14 may also activate the control program 192 on the user mobile device 180, at which point the user mobile device 180 may begin communicating with the apparatus 10 over the network 30 as discussed above with reference to FIG. 31. In some embodiments, the user mobile device 180 may also begin communicating with the server 202 of the network 30.

In a second step 404 of the method 400, the user mobile device 180 may retrieve one or more selectable programmed sessions (e.g., the programmed sessions 320 depicted with reference to FIG. 33). In some embodiments, the programmed sessions 320 are stored in the memory 188 of the user mobile device 180. In other embodiments, the programmed sessions are stored in the database 210 of the server 202, and therefore the user mobile device 180 may communicate with the server 202 over the network 30 to retrieve the programmed sessions. In some cases of such embodiments, the user mobile device 180 simply retrieves an identification of each of the applicable programmed sessions 320 from the server 202. In other cases of such embodiments, the user mobile device 180 receives the entirety of the programmed session from the server 202 (e.g., a collection of data packets 310 as depicted with reference to FIG. 32) in order to display the programmed sessions 320.

In a third step 406 of the method 400, the user mobile device 180 may display the retrieved programmed sessions 320 via the user interface 194, as depicted with reference to FIG. 33.

In a fourth step 408 of the method 400, the user mobile device 180 may receive an indication from the user 14 selecting one of the programmed sessions 320. For example, the user 14 may select "Session A" on the graphical user interface 194 depicted with reference to FIG. 33.

In a fifth step 410 of the method 400, the user mobile device 180 may transmit the selected programmed session 320 to the apparatus 10. In some embodiments, as mentioned above, the data (e.g., a number of data packets 310 depicted with reference to FIG. 32) associated with the programmed sessions 320 may be stored in the memory 188 of the user mobile device 180 (whether the data associated with the programmed sessions 320 are always stored in the memory 188, or the data associated with the programmed sessions 320 were received in their entirety from the server 202 pursuant to displaying the various programmed sessions 320 as depicted with reference to FIG. 32), and thus be directly transmitted from the user mobile device 180 to the apparatus 10. In other embodiments, and as suggested above, the data associated with the programmed sessions 320 may be stored in the database 210 of the server 202 as of the step 410. In some cases of such embodiments, the user mobile device 180 may communicate with the server 202 over the network 30 to retrieve the data associated with the selected programmed session 320 in the form of the data packets 310, and then transmit the data packets 310 to the apparatus 10. In other cases of such embodiments, the user mobile device 180 may communicate with the server 202, directing the server 202 to begin transmitting the data packets 310 associated with the selected programmed session 320 to the apparatus 10.

In a sixth step 412 of the method 400, the apparatus 10 may be operated in accordance with the selected programmed session 320. As suggested above, the apparatus 10 may receive data packets 310 associated with the selected programmed session 320 from the user mobile device 180 or the server 202. In some embodiments, as each data packet 310 is received by the apparatus 10, the apparatus 10 may immediately be controlled in accordance with the data packet 310 until a new data packet 310 is received that changes the control of the apparatus 10. In other words, the apparatus 10 may begin "streaming" the selected programmed session 320 from the user mobile device 180 or the server 202. In other embodiments, all of the data packets 310 associated with the selected programmed session 320 may be received by the apparatus 10 from the user mobile device 180 or the server 202 before the apparatus 10 begins functioning in accordance with the selected programmed session 320. The data packets 310 may be stored, at least temporarily, in the memory 156 of the apparatus 10, and once the complete selected programmed session 320 is stored in the memory 156 of the apparatus 10, the apparatus 10 may begin functioning in accordance with the programmed session. In other words, the apparatus 10 may "download" the data associated with the selected programmed session 320 and function accordingly upon completion of the download.

Figure 35:
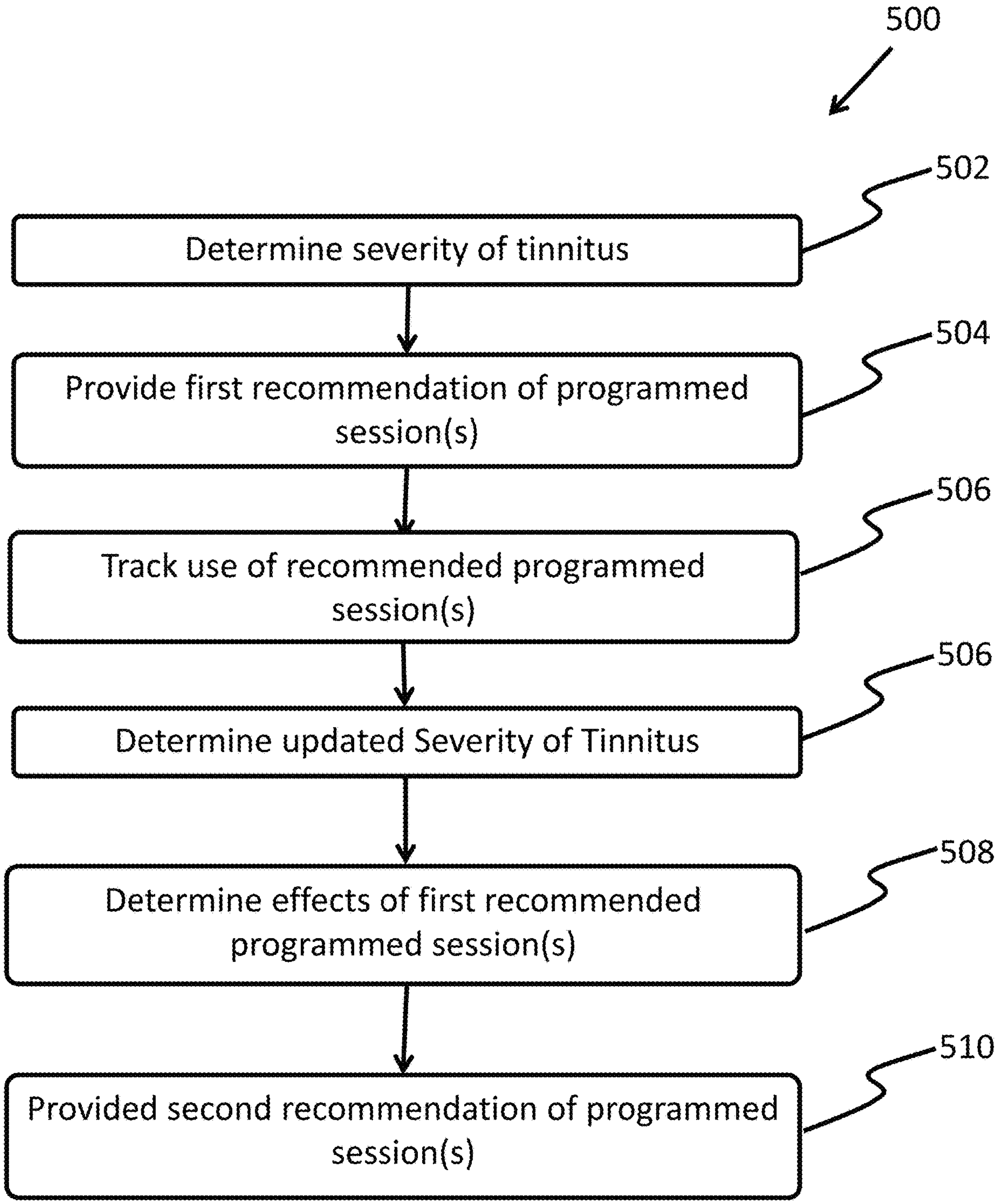
FIG. 35 is a flow diagram of a method of treating tinnitus in accordance with the present disclosure.

Referring now to FIG. 35, the control program 192 of the user mobile device 180 may facilitate a method 500 of determining the severity of tinnitus in the user 14, recommending various programmed sessions for the purpose of treating and/or masking the tinnitus, and determining the effectiveness of the various programmed sessions.

In a first step 502 of the method 500, the control program 192 may determine the severity of the tinnitus exhibited by the user 14. In some embodiments, the control program 192 of the user mobile device 180, via the user interface 194, may provide the user 14 with various GUIs facilitating a questionnaire in order to evaluate the tinnitus of the user 14 (e.g., the severity of the tinnitus of the user 14). As a first example, the questionnaire may simply allow the user 14 to rate their perceived impact of tinnitus (e.g., how bad is the perceived ringing of the user 14 due to tinnitus, how well does the user 14 hear in spite of tinnitus, etc.) on a subjective "one-to-ten" scale. As a second example, the questionnaire may provide various circumstantial questions that are evaluated by the control program 192 in order to evaluate the tinnitus of the user 14.

In other embodiments, the control program 192 of the user mobile device 180 may provide the user 14 with various GUIs facilitating a test in order to evaluate the tinnitus of the user 14. For example, the test may be provided in the form of a hearing exercise to determine the severity of the tinnitus of the user 14. In this sense, the user mobile device 180 may transmit a series of sounds or tones of various frequencies and/or volumes, and the user can respond as to their recognition of the sounds (e.g., pressing a button every time the user 14 hears a tone, providing an input identifying how many times the user perceived a tone over a span of time, etc.). The test tones may be provided to the user 14 over a set of head-phones in communication with the user mobile device 180.

In other embodiments, the control program 192 may provide, as one of the programmed sessions 320 displayed with reference to FIG. 32, a "trial" session that the user 14 may review (e.g., provide a rating) with regard to its perceived effectiveness for treatment and/or masking. Such trial sessions may further include a determination of the first and second auditory thresholds of the user 14 for recommending an optimal volume setting. As mentioned above, a first auditory threshold for low frequency tones may be determined for the user 14, such that an optimal volume may be recommended at a level that is about five to ten decibels above the first auditory threshold. Similarly, a second auditory threshold for high frequency tones may be determined for the user 14, such that an optimal volume for high frequency tones may be recommended at a level that is about five to ten decibels above the second auditory threshold. In this sense, the trial session may use various volumes, and the user 14 may provide a response when the user 14 is able to perceive the volume for high and low frequency tones.

In some embodiments, the questionnaire, test, or trial session may correspond to standard methodologies applied in clinical settings (e.g., otolaryngological studies). In other embodiments, the questionnaire, test, or programmed session may be generated independently of such clinical methodologies.

In some embodiments, the control program 192 may use the questionnaire, test, and/or trial session in order to determine the Tinnitus Handicap Inventory (THI) index of the user 14. For example, the THI index of the user 14 may be a numeric score between zero and one-hundred. A score of zero to sixteen indicates no or slight handicap related to tinnitus, a score of eighteen to thirty-six indicates a mild handicap related to tinnitus, a score of thirty-eight to fifty-six indicates a moderate handicap related to tinnitus, a score of fifty-eight to seventy-six indicates a severe handicap related to tinnitus, and a score of seventy-eight to one-hundred indicates a catastrophic handicap related to tinnitus. In other embodiments, the control program 192 may determine other variables in order to index the particular severity and/or circumstances of the tinnitus suffered by the user 14.

In some embodiments, the control program 192 may communicate with the server 202 in order to determine the severity of the tinnitus of the user 14. For example, the server 202 may accumulate data (stored in the database 210) that correlates responses to the questionnaire, test, and/or trial session and the severity of tinnitus of the user 14. Such data may not only include the responses to the questionnaire, test, and/or trial session by the user 14, but also responses by other users who use the control program 192 and the apparatus 10, as well as other clinical data accumulated by the server 202.

In a step 504 of the method 500, the control program 192 may provide a recommendation of programmed sessions for operation of the apparatus 10 in order to treat and/or mask tinnitus in the user 14. For example, the control program 192 may at least partially populate the programmed sessions 320 depicted with reference to FIG. 33 with programmed sessions that are known to be effective for individuals with similar results to the questionnaire, test, and/or trial session applied at step 502. In some embodiments, the recommendation of programmed sessions is received from the server 202, as suggested above. In other embodiments, the data corresponding to such recommendable programmed sessions is stored directly on the user mobile device 180 (e.g., in the memory 188).

In a step 506 of the method 500, the control program 192 may track the use of the programmed session(s) recommended to the user 14 in accordance with the steps above. For example, the control program 192 may record each use of the recommended programmed session(s) by the user 14 (as opposed to using other pre-set programmed sessions, manual control of the apparatus 10, etc.). In some embodiments, the control program 192 stores such data in the memory 188. In other embodiments, the control program 192 provides records of such data to the server 202, to be stored in the database 210 in a data store associated with the user 14.

In a step 508 of the method 500, the control program 192 and/or the server 202 may make an updated determination of the severity of the tinnitus experienced by the user 14. For example, the questionnaire, test, and/or trial session may be periodically repeated presented to the user 14 by the control program 192. As suggested above, such results may be transmitted to the server 202 for an actual determination of the updated severity of the tinnitus experienced by the user 14.

In a step 508 of the method 500, the control program 192 and/or the server 202 may determine the effectiveness of the programmed session(s) recommended the step 504. For example, the severity of the tinnitus determined at the step 507 may be compared to the severity of the tinnitus determined at the step 502 (e.g., improvement, worsening, remaining the same, etc.). This comparison may further be cross-referenced with the data accumulated with respect to the programmed sessions recommended at the step 506 (in addition to any other programmed sessions or manual operations used by the user 14 since the severity determination made at the step 502). Accordingly, any improvements, worsening, or otherwise may be correlated with the particular use the user 14 has made of the apparatus 10, including any programmed sessions previously recommended at the step 504, other programmed sessions created and used by the user 14, or other manual operations of the apparatus 10. Such data may be transmitted and/or processed by the server 202 (or, in other embodiments, independently on the user mobile device 180) for improvements to the various programmed sessions recommended to the user 14. As a first example, the processing may be done on an individual basis. In this sense, the improvements, worsening, or otherwise of the tinnitus experienced by the user 14 may be individually processed with respect to the use of the user 14, determining the effectiveness of the various programmed sessions and manual operations used by the user 14 in treating and/or masking tinnitus. As a second example, the processing may be done on an aggregate basis. In this sense, the data associated with the user 14 may be compared and correlated with data associated with other users of the apparatus 10 and the control program 192.

In any case, such processing of data may be associated with artificial intelligence, machine learning, or otherwise. For example, the server 202 may train a machine learning model in accordance with the data accumulated in accordance with the steps above. The machine learning model may develop training data in the form of the use of the user 14 and/or other users (a first determination of severity, recommended programmed sessions used, other programmed sessions used, manual operations used, and a second determination of severity). The machine learning model may ingest the training data in order to compile a learned model that associates a user's severity or other symptoms associated with tinnitus and ensuing use of the apparatus 10 with results (e.g., changes to the user's severity or other symptoms associated with tinnitus).

In a step 510 of the method 500, the control program 192 may provide the user 14 with an updated recommendation of programmed sessions to be displayed as one or more of the programmed sessions 320 depicted with reference to FIG. 33. As discussed above, such updated recommendations may be the output of the ever-improving machine learning model developed in accordance with the step 508. In other embodiments may be an independent determination provided by the control program 192 using data stored in the memory 188.

Thus, although there have been described particular embodiments of the present invention of a new and useful APPARATUS AND METHODS FOR TREATING TINNITUS it is not intended that such references be construed as limitations upon the scope of this invention.

What is claimed is:

1. An apparatus for treating tinnitus, the apparatus comprising:

a strap configured to be positioned about a head of a user; and a plurality of bone conductors attached to the strap, the plurality of bone conductors including:

a first low frequency bone conductor configured to contact the head of the user rearward of a first ear of the user, and a second low frequency bone conductor configured to contact the head of the user rearward of a second ear of the user, wherein the first low frequency bone conductor and the second low frequency bone conductor are each configured to generate tones at a frequency between about fifty hertz and about one-hundred-and-ten hertz, wherein the plurality of bone conductors further includes:

a first high frequency bone conductor configured to contact the head of the user forward of the first ear of the user, and a second high frequency bone conductor configured to contact the head of the user forward of the second ear of the user, and wherein the first high frequency bone conductor and the second high frequency bone conductor are each configured to generate tones at a frequency of between about six-thousand hertz and ten-thousand hertz.

2. The apparatus of claim 1, wherein the strap is configured to be positioned over a top of the head of the user.

3. The apparatus of claim 2, wherein a length of the strap is adjustable, and an orientation of the strap is adjustable.

4. The apparatus of claim 3, further comprising:

a first hinge located between the first low frequency bone conductor and the first high frequency bone conductor, the first hinge configured to adjust an orientation of the first high frequency bone conductor relative to the strap; and a second hinge located between the second low frequency bone conductor and the second high frequency bone conductor, the second hinge configured to adjust an orientation of the second high frequency bone conductor relative to the strap.

5. A method of treating tinnitus, the method comprising:

positioning a headset apparatus on a head of a user;

administering low frequency tones using a first pair of bone conductors of the headset apparatus for a predetermined time period, the low frequency tones being between about fifty hertz and one-hundred-and-ten hertz; and simultaneously administering high frequency tones using a second pair of bone conductors of the headset apparatus for the predetermined time period, the high frequency tones being between about six-thousand hertz and about ten-thousand hertz.

6. The method of claim 5, further comprising:

determining a first subjective auditory threshold of the user for the low frequency tones; and determining a second subjective auditory threshold of the user for the high frequency tones, wherein the low frequency tones are administered at a volume above the first subjective auditory threshold and the high frequency tones are administered at a volume above the second subjective auditory threshold.

7. The method of claim 6, wherein the volume of the low frequency tones are administered at about five to about ten decibels above the first subjective auditory threshold and the volume of the high frequency tones are administered at about five to ten decibels above the second subjective auditory threshold.

8. The method of claim 5, wherein administering the low frequency tones includes sweeping the low frequency tones back and forth between about fifty hertz and one-hundred-and-ten hertz during the pre-determined time period.

9. The method of claim 5, wherein the pre-determined time period is up to one minute.

10. The method of claim 5, wherein the pre-determined time period is up to fifteen minutes.

11. A system for treating tinnitus, the system comprising:

a headset apparatus, the headset apparatus including:

a strap configured to be positioned about a head of a user; and a plurality of bone conductors, the plurality of bone conductors including:

a first low frequency bone conductor configured to contact the head of the user rearward of a first ear of the user, and a second low frequency bone conductor configured to contact the head of the user rearward of a second ear of the user; and a controller configured to control a volume and a frequency of tones generated by each of the first and the second low frequency bone conductors, wherein the first low frequency bone conductor and the second low frequency bone conductor are each configured to generate the frequency of tones at a between about fifty hertz and about one-hundred-and-ten hertz, wherein the plurality of bone conductors further includes:

a first high frequency bone conductor configured to contact the head of the user forward of the first ear of the user, and and a second high frequency bone conductor configured to contact the head of the user forward of the second ear of the user, wherein the controller is further configured to control a volume and a frequency of tones generated by each of the first and the second high frequency bone conductors, and wherein the first high frequency bone conductor and the second high frequency bone conductor are each configured to generate the frequency of tones between about six-thousand hertz and ten-thousand hertz.

12. The system of claim 11, wherein the strap is configured to be positioned over a top of the head of the user.

13. The system of claim 11, wherein the controller is located within the headset apparatus, the headset apparatus further including a frequency control and a volume control, the frequency control configured to receive a manual frequency control input and communicate the manual frequency control input to the controller, the volume control configured to receive a manual volume control input and communicate the manual volume control input to the controller, and wherein the controller is further configured to control the volume and the frequency of tones generated by the plurality of bone conductors based on the manual volume control input and the manual frequency control input.

14. The system of claim 13, wherein the headset apparatus further includes a channel selector, the channel selector configured to receive a channel selection input and communicate the channel selection input to the controller, and wherein the controller is further configured to, in response to the channel selection input, alternate application of the manual frequency control input and the manual volume control input between the plurality of bone conductors.

15. The system of claim 11, wherein the controller is located within an external device apart from the headset apparatus, the external device including a frequency control, a volume control, and a wired connection extending between the controller and the headset apparatus, the frequency control configured to receive a manual frequency control input on the external device and communicate the manual frequency control input to the controller, the volume control configured to receive a manual volume control input on the external device and communicate the manual volume control input to the controller, and wherein the controller is further configured to control, via the wired connection, the volume and the frequency of tones generated by the plurality of bone conductors based on the manual volume control input and the manual frequency control input.

16. The system of claim 15, wherein the external device further includes a channel selector, the channel selector configured to receive a channel selection input on the external device, and wherein the controller is further configured to, in response to the channel selection input, alternate application of the manual frequency control input and the manual volume control input between the plurality of bone conductors.

17. The system of claim 11, further comprising a mobile device, wherein the controller is located within the headset apparatus, the mobile device is configured to receive one or more mobile device inputs, and based on the one or more mobile device inputs, wirelessly transmit one or more messages to the controller, and wherein the controller is further configured to control the volume and the frequency of tones generated by the plurality of bone conductors based on the one or more messages wirelessly received from the mobile device.

18. The system of claim 17, wherein the one or more mobile device inputs includes a selection of a pre-configured programmed session, the pre-configured programmed session associated with a plurality of pre-set frequency control inputs and volume control inputs over a pre-determined period of time, and wherein the mobile device is further configured to wirelessly transmit the one or more messages to the controller in accordance with the pre-configured programmed session.

* * * * *